United States Patent
Ribas et al.

(10) Patent No.: US 10,201,597 B2
(45) Date of Patent: Feb. 12, 2019

(54) CODON-OPTIMIZED LENTIVIRAL VECTOR FOR STEM CELL REPROGRAMMING

(71) Applicant: The Regents of the University of California, Oakland, CA (US)

(72) Inventors: Antoni Ribas, Los Angeles, CA (US); Richard C. Koya, Buffalo, NY (US); Thinle Chodon, Buffalo, NY (US)

(73) Assignee: The Regents of the University of California, Oakland, CA (US)

( * ) Notice: Subject to any disclaimer, the term of this patent is extended or adjusted under 35 U.S.C. 154(b) by 121 days.

(21) Appl. No.: 15/516,012

(22) PCT Filed: Sep. 29, 2015

(86) PCT No.: PCT/US2015/053010
§ 371 (c)(1),
(2) Date: Mar. 30, 2017

(87) PCT Pub. No.: WO2016/054086
PCT Pub. Date: Apr. 7, 2016

(65) Prior Publication Data
US 2018/0326033 A1 Nov. 15, 2018

Related U.S. Application Data

(60) Provisional application No. 62/057,397, filed on Sep. 30, 2014.

(51) Int. Cl.
*A61K 39/00* (2006.01)
*C07K 14/725* (2006.01)
*C12N 15/86* (2006.01)

(52) U.S. Cl.
CPC .. *A61K 39/001188* (2018.08); *C07K 14/7051* (2013.01); *C12N 15/86* (2013.01); *A61K 2039/5156* (2013.01); *A61K 2039/876* (2018.08); *C12N 2740/15043* (2013.01)

(58) Field of Classification Search
None
See application file for complete search history.

(56) References Cited

U.S. PATENT DOCUMENTS

| 2008/0199424 A1 | 8/2008 | Yang et al. |
| 2009/0053184 A1 | 2/2009 | Morgan et al. |
| 2011/0038842 A1 | 2/2011 | Boulter et al. |

OTHER PUBLICATIONS

Gschweng, E.H., et al., 'HSV-sr39TK positron emission tomography and suicide gene elimination of human hematopoietic stem cells and their progeny in humanized mice', Cancer Research, Sep. 15, 2014, vol. 74, No. 18, pp. 5173-5183.
NCBI, GenBank Accession No. JN180298.1, 'Synthetic construct TRBV6-5 (TRBV6-5) gene, partial cds', Nov. 3, 2011.
PCT International Search Report and Written Opinion dated Jan. 26, 2016, PCT Application No. PCT/US2015/053010.

*Primary Examiner* — Catherine S Hibbert
(74) *Attorney, Agent, or Firm* — Gates & Cooper LLP

(57) ABSTRACT

The invention relates to methods and materials that can be used to product cytotoxic T cells that target cancer cells expressing the cancer-testis antigen NY ESO-1. Illustrative embodiments of the invention include peripheral blood stem cells transduced with a lentiviral vector that comprises a codon optimized TCR alpha and beta chain polypeptides specific for NY ESO-1. These gene-modified cells are useful, for example, in a hematopoietic stem cell transplantation setting to treat patients diagnosed with NY ESO-1 positive cancers.

21 Claims, 17 Drawing Sheets
Specification includes a Sequence Listing.

3A
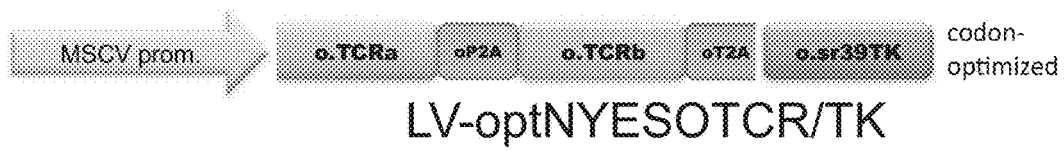
LV-optNYESOTCR/TK
3B
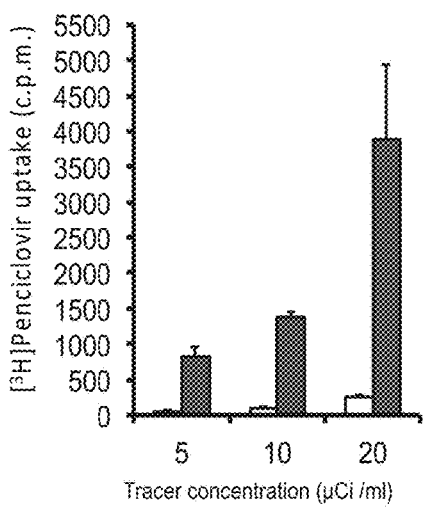
3C
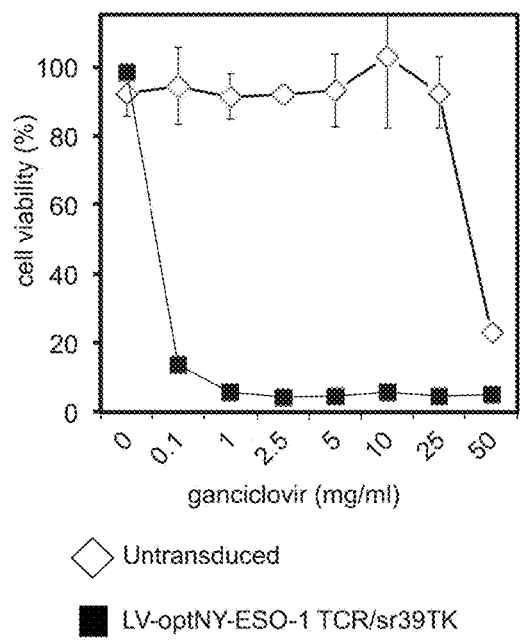
FIGS. 3A-C

5A
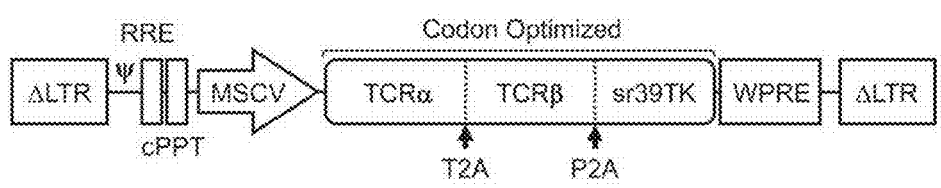
5B
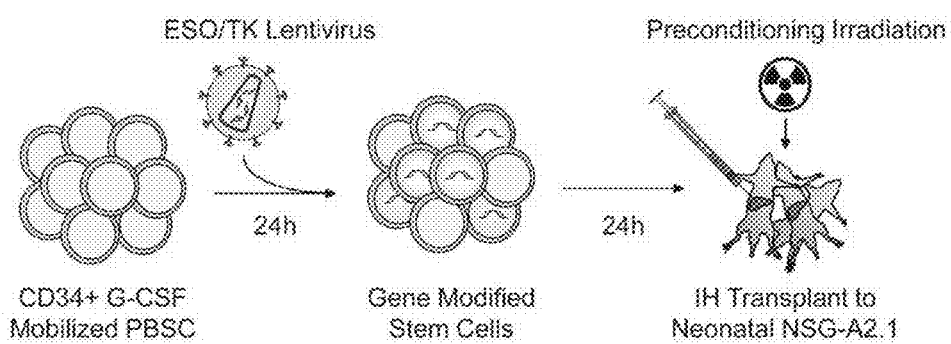
5C
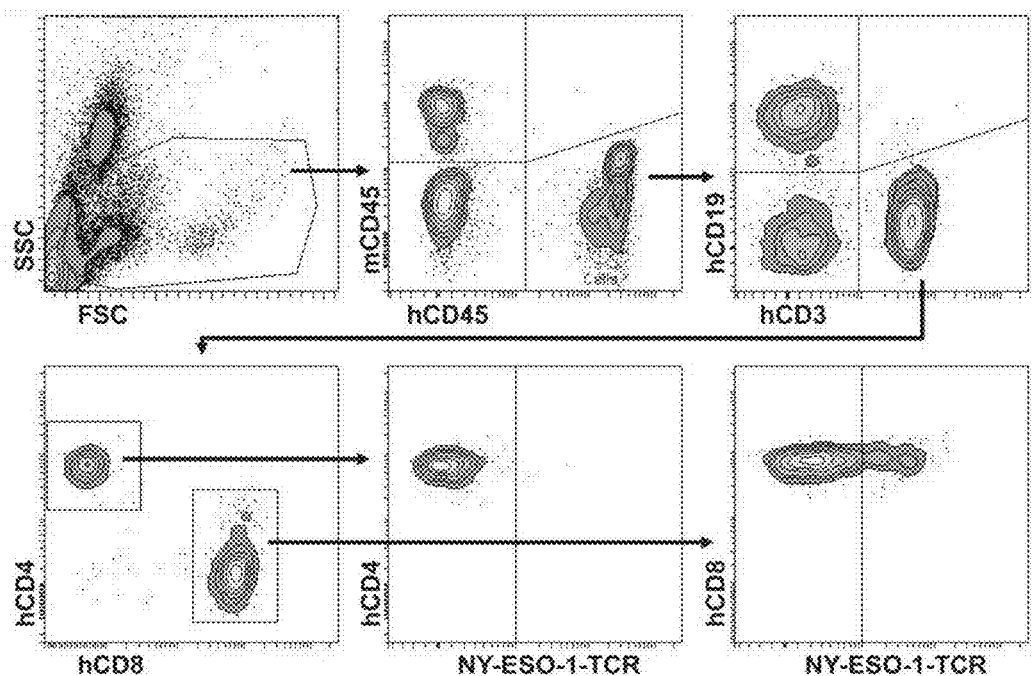
FIGS. 5A-C

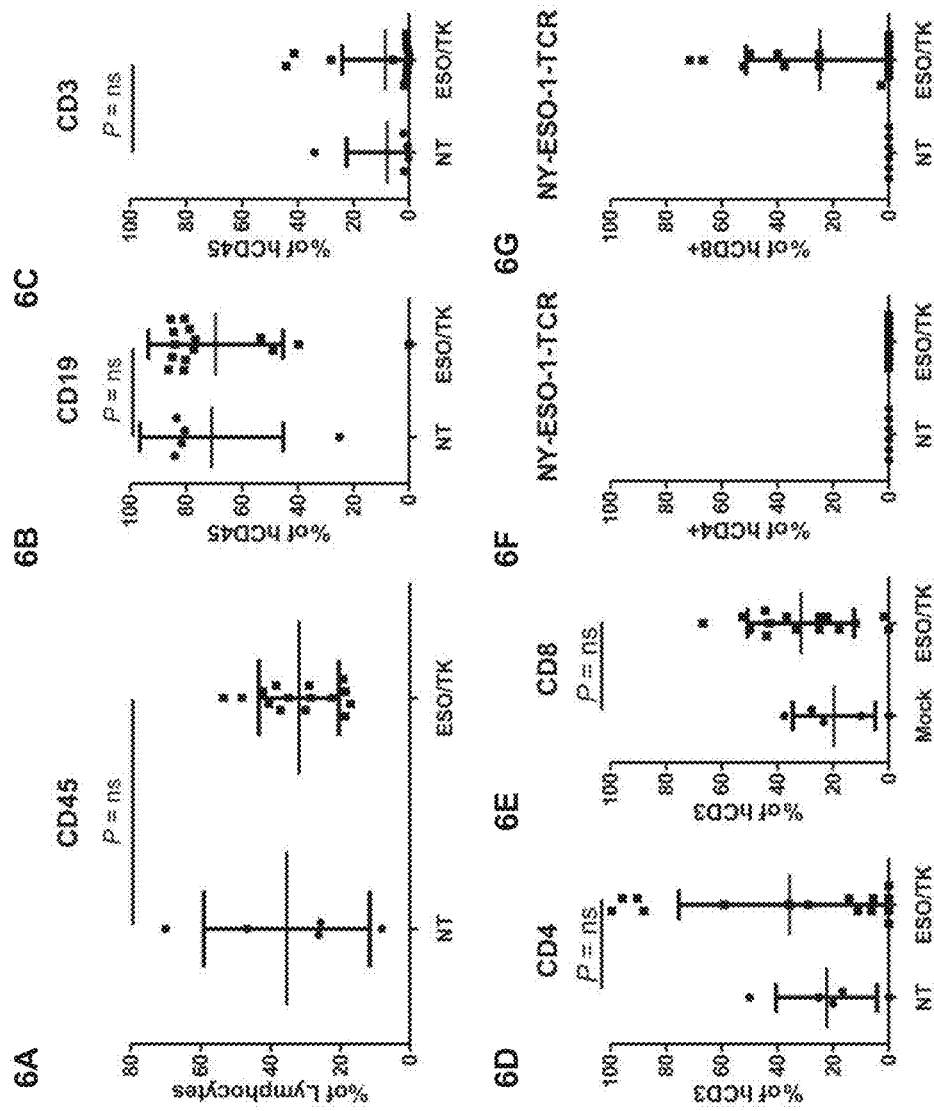
FIGS. 6A-G

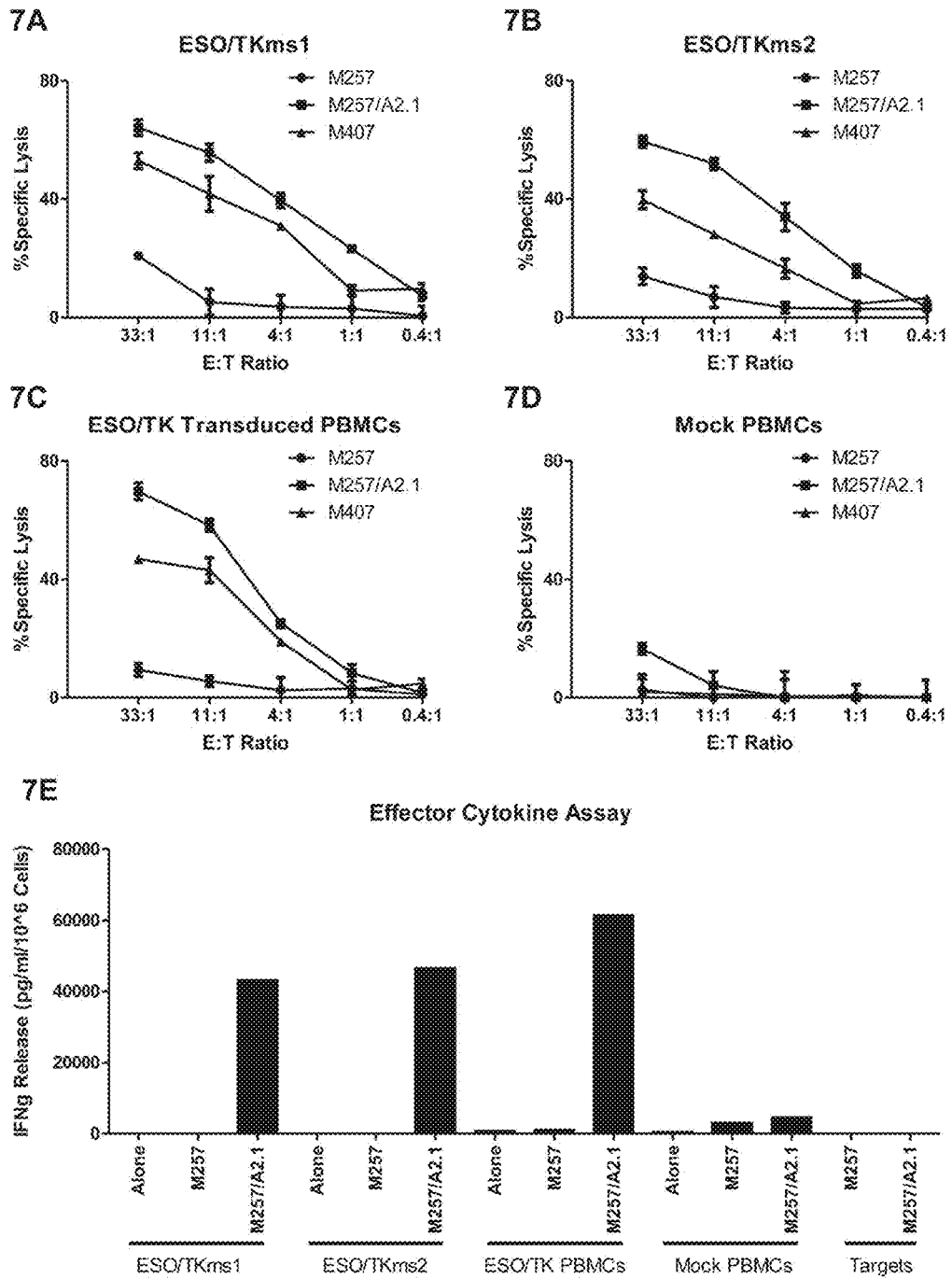
FIGS. 7A-E

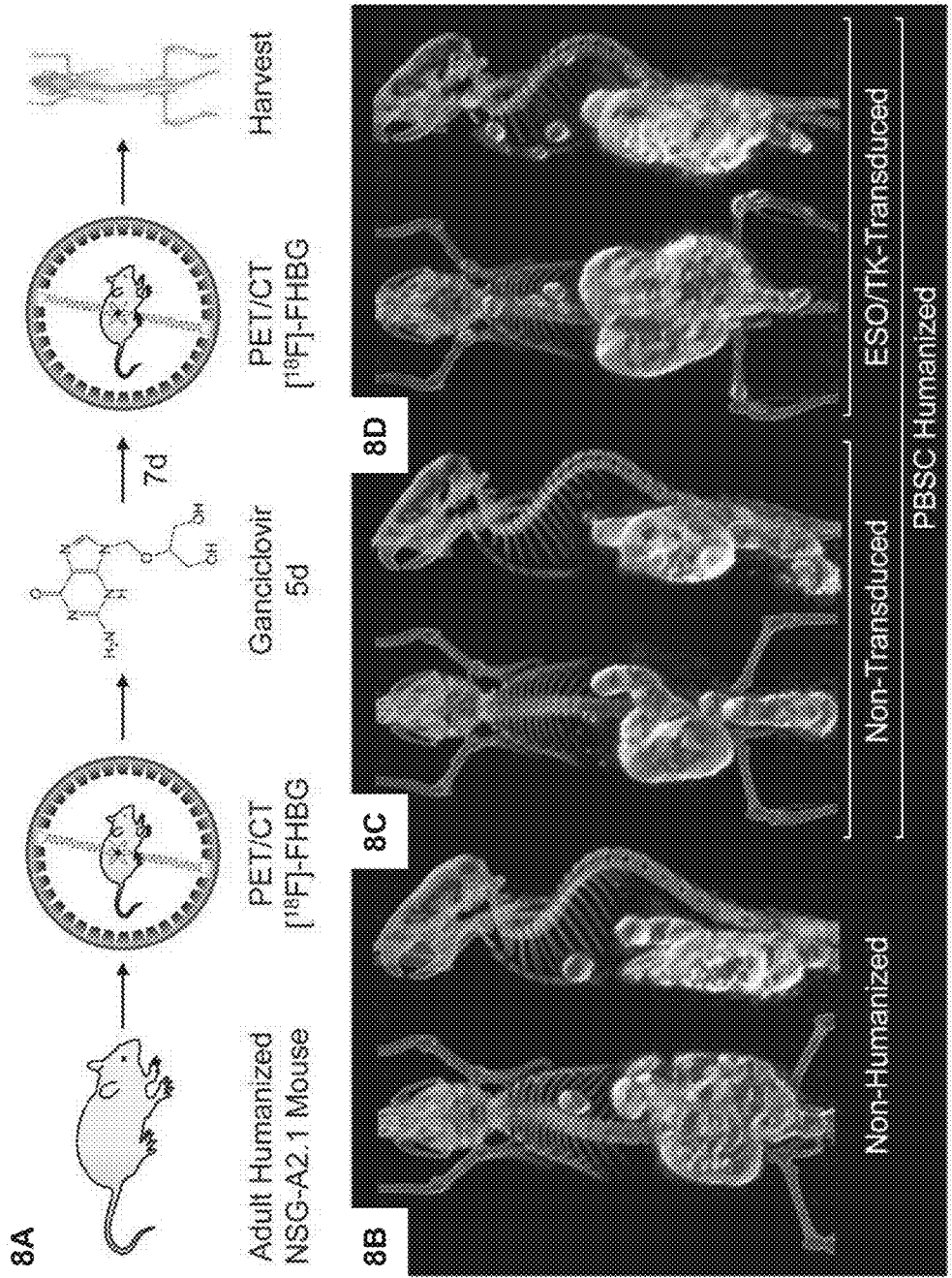
FIGS. 8A-D

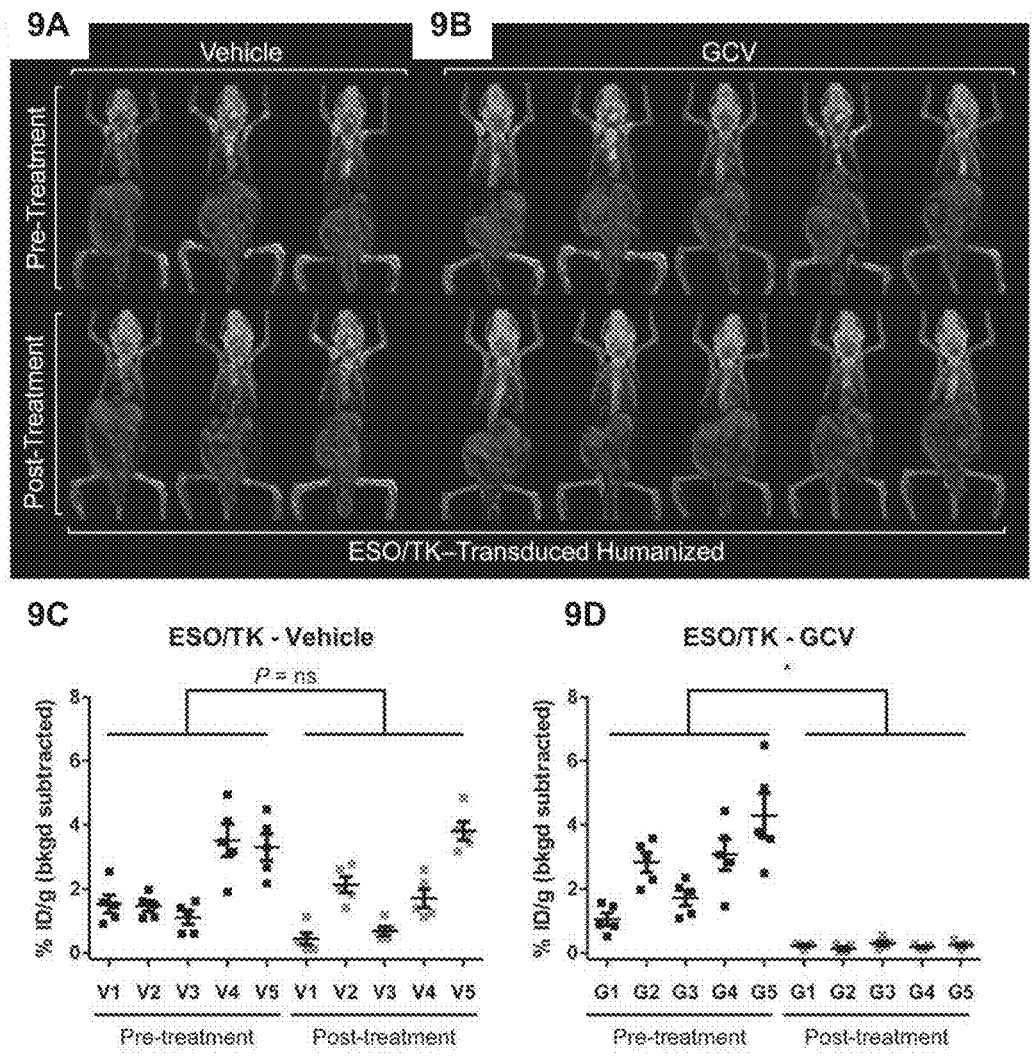
FIGS. 9A-D

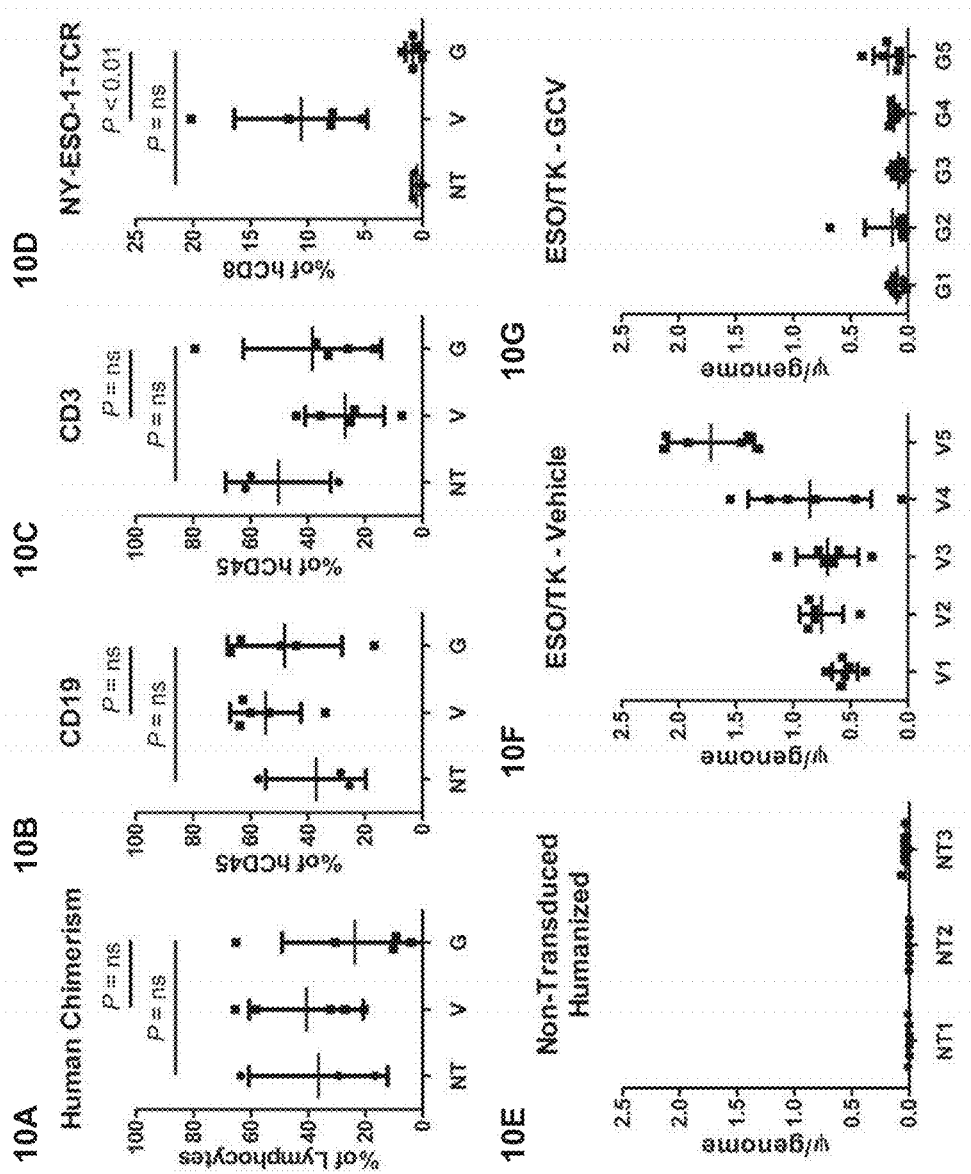
FIGS. 10A-G

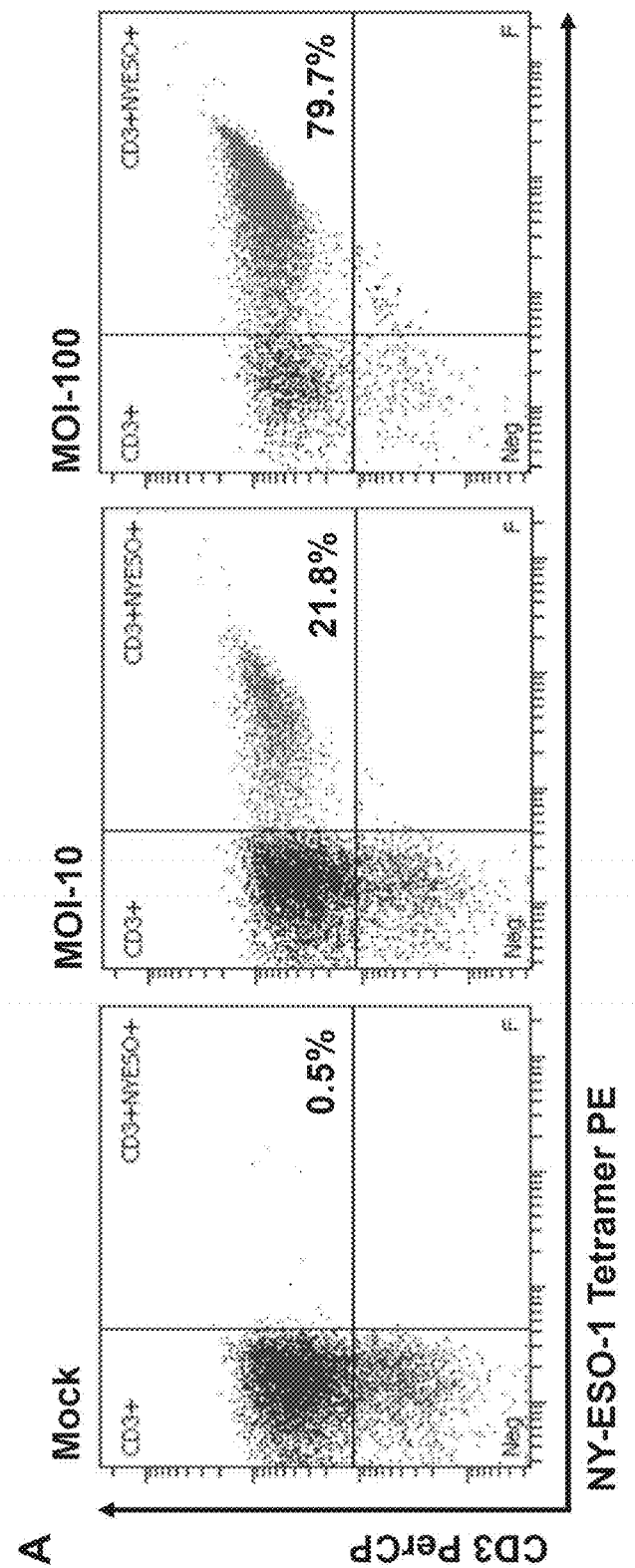

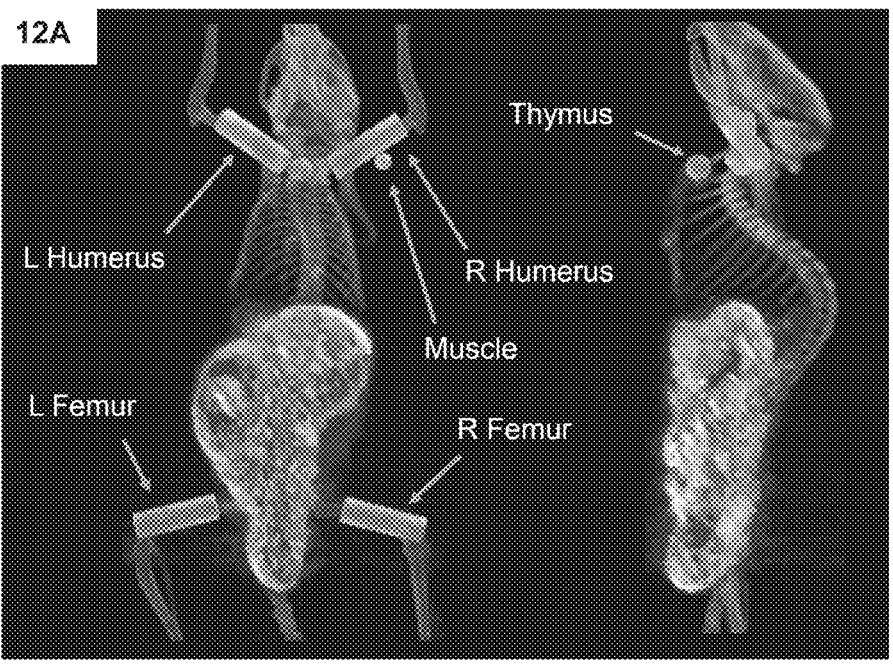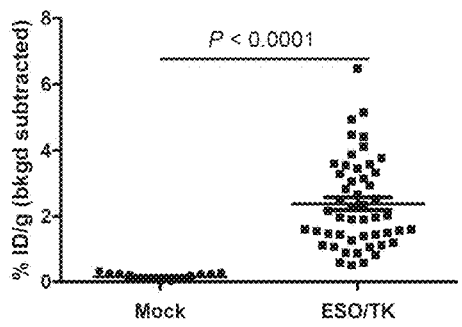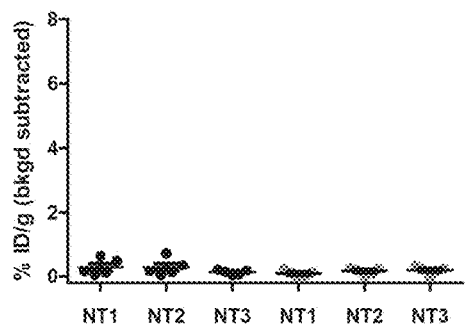
FIGS. 12A-C

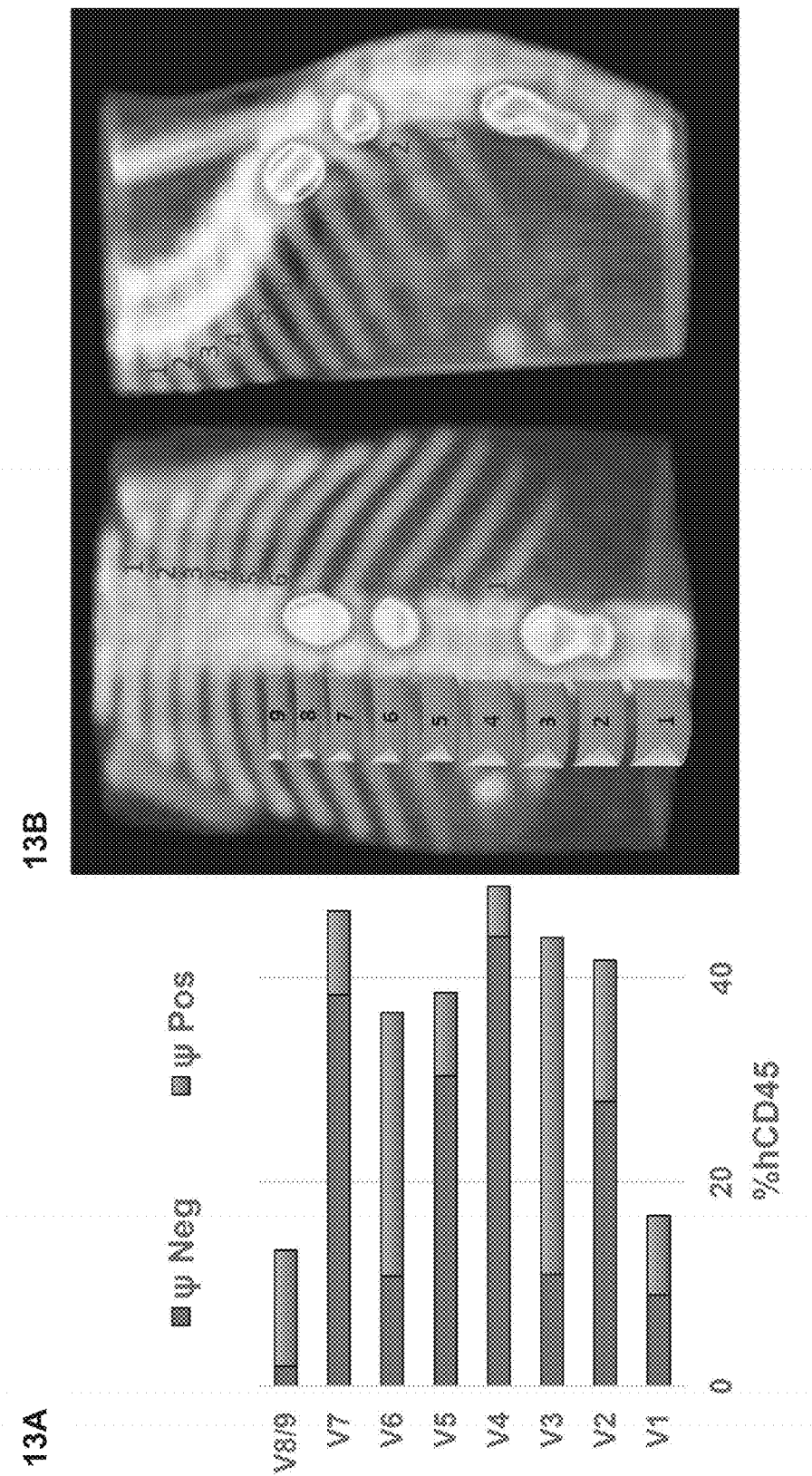
FIGS. 13A-B

SEQUENCE LISTING

<160> NUMBER OF SEQ ID NOS: 11

<210> SEQ ID NO 1
<211> LENGTH: 822
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
atggaaacac tgctgggcct gctgatcctg tggctgcagc tgcagtgggt gtccagcaag    60
caggaagtga cccagatccc tgccgccctg tctgtgcctg agggcgagaa cctggtgctg   120
aactgcagct tcaccgacag cgccatctac aacctgcagt ggttcagaca ggaccccggc   180
aagggcctga caagcctgct gctgattcag agcagccaga gagagcagac cagcggcaga   240
ctgaacgcca gcctggataa gagcagcggc cggtccaccc tgtatatcgc cgcttctcag   300
cctggcgact ccgccacata tctgtgtgct gtgcggcctc tgtacggcgg cagctacatc   360
cctaccttcg gcagaggcac cagcctgatc gtgcacccct acatccagaa ccccgacccc   420
gccgtgtacc agctgagaga cagcaagtcc agcgacaaga gcgtgtgcct gttcaccgac   480
ttcgacagcc agaccaacgt gtcccagagc aaggacagcg acgtgtacat caccgacaag   540
accgtgctgg acatgcggag catggacttc aagagcaaca cgccgtggc ctggtccaac   600 aagagcgatt cgcctgcgc caacgccttc aacaacagca ttatccccga ggacacattc   660
ttcccaagcc ccgagagcag ctgcgacgtg aagctggtgg aaaagagctt cgagacagac   720
accaacctga acttccagaa cctgagcgtg atcggcttcc ggattctgct gctgaaggtg   780
gccggcttca acctgctgat gaccctgaga ctgtggtcca gc                      822
```

<210> SEQ ID NO 2
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
            100                 105                 110

Pro Leu Tyr Gly Gly Ser Tyr Ile Pro Thr Phe Gly Arg Gly Thr Ser
        115                 120                 125

Leu Ile Val His Pro Tyr Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160
```

```
Phe Asp Ser Gln Thr Asn Val Ser Gln Ser Lys Asp Ser Asp Val Tyr
            165                 170                 175

Ile Thr Asp Lys Thr Val Leu Asp Met Arg Ser Met Asp Phe Lys Ser
        180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
            245                 250                 255

Leu Leu Lys Val Ala Gly Phe Asn Leu Leu Met Thr Leu Arg Leu Trp
            260                 265                 270

Ser Ser
```

<210> SEQ ID NO 3
<211> LENGTH: 925
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
atgagcatcg gcctgctgtg ttgtgccgct ctgtccctgc tgtgggccgg acctgtgaat    60
gctggcgtga cacagacccc caagttccag gtgctgaaaa ccggccagag catgaccctg   120
cagtgcgccc aggacatgaa ccacgagtac atgagctggt atcggcagga ccctggcatg   180
ggactgcggc tgatccacta ctctgtgggc gccggcatca ccgatcaggg cgaggtgccc   240
aacggctaca atgtgtccag atccaccacc gaggacttcc cactgagact gctgtctgcc   300
gcccctagcc agacctccgt gtacttctgt gccagcagct acgtgggcaa caccggcgag   360
ctgttctttg gcgagggcag cagactgaca gtgctggaag atctgaagaa cgtgttcccc   420
ccagaggtgg ccgtgttcga gccttctgag gccgagatca gccacaccca gaaagccacc   480
ctcgtgtgtc tggccaccgg cttctacccc gaccacgtgg aactgtcttg gtgggtcaac   540
ggcaaagagg tgcacagcgg cgtgtccacc gatccccagc tctgaaagag cagcccgcc   600 ctgaacgaca gccggtactg tctgtcctcc cggctgagag tgtccgccac cttctggcag   660
aaccccggga accacttcag atgccaggtg cagttctacg gcctgagcga aaacgacgag   720
tggacccagg acagagccaa gcccgtgact cagatcgtgt ctgccgaggc tggggcaga   780 gccgattgtg gctttaccag cgagagctac cagcagggcg tgctgagcgc caccatcctg   840
tacgagatcc tgctgggcaa ggccaccctg tacgccgtgc tggtgtccgc cctggtgctg   900
atggccatgg tcaaacggaa ggact                                         925
```

<210> SEQ ID NO 4
<211> LENGTH: 308
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Met Ser Ile Gly Leu Leu Cys Cys Ala Ala Leu Ser Leu Leu Trp Ala
1               5                   10                  15
Gly Pro Val Asn Ala Gly Val Thr Gln Thr Pro Lys Phe Gln Val Leu
            20                  25                  30
Lys Thr Gly Gln Ser Met Thr Leu Gln Cys Ala Gln Asp Met Asn His
        35                  40                  45
Glu Tyr Met Ser Trp Tyr Arg Gln Asp Pro Gly Met Gly Leu Arg Leu
    50                  55                  60
Ile His Tyr Ser Val Gly Ala Gly Ile Thr Asp Gln Gly Glu Val Pro
65                  70                  75                  80
Asn Gly Tyr Asn Val Ser Arg Ser Thr Thr Glu Asp Phe Pro Leu Arg
                85                  90                  95
Leu Leu Ser Ala Ala Pro Ser Gln Thr Ser Val Tyr Phe Cys Ala Ser
            100                 105                 110
Ser Tyr Val Gly Asn Thr Gly Glu Leu Phe Phe Gly Glu Gly Ser Arg
        115                 120                 125
Leu Thr Val Leu Glu Asp Leu Lys Asn Val Phe Pro Pro Glu Val Ala
    130                 135                 140
Val Phe Glu Pro Ser Glu Ala Glu Ile Ser His Thr Gln Lys Ala Thr
145                 150                 155                 160
Leu Val Cys Leu Ala Thr Gly Phe Tyr Pro Asp His Val Glu Leu Ser
                165                 170                 175
Trp Trp Val Asn Gly Lys Glu Val His Ser Gly Val Ser Thr Asp Pro
            180                 185                 190
Gln Pro Leu Lys Glu Gln Pro Ala Leu Asn Asp Ser Arg Tyr Cys Leu
        195                 200                 205
Ser Ser Arg Leu Arg Val Ser Ala Thr Phe Trp Gln Asn Pro Arg Asn
    210                 215                 220
His Phe Arg Cys Gln Val Gln Phe Tyr Gly Leu Ser Glu Asn Asp Glu
225                 230                 235                 240
Trp Thr Gln Asp Arg Ala Lys Pro Val Thr Gln Ile Val Ser Ala Glu
                245                 250                 255
Ala Trp Gly Arg Ala Asp Cys Gly Phe Thr Ser Glu Ser Tyr Gln Gln
            260                 265                 270
Gly Val Leu Ser Ala Thr Ile Leu Tyr Glu Ile Leu Leu Gly Lys Ala
        275                 280                 285
Thr Leu Tyr Ala Val Leu Val Ser Ala Leu Val Leu Met Ala Met Val
    290                 295                 300
Lys Arg Lys Asp
305
```

<210> SEQ ID NO 5
<211> LENGTH: 9442
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
agcttaatgt agtcttatgc aatactcttg tagtcttgca acatggtaac gatgagttag      60
caacatgcct tacaaggaga gaaaaagcac cgtgcatgcc gattggtgga agtaaggtgg     120
tacgatcgtg ccttattagg aaggcaacag acgggtctga catggattgg acgaaccact     180
```

```
gaattgccgc attgcagaga tattgtattt aagtgcctag ctcgatacat aaacgggtct    240
ctctggttag accagatctg agcctgggag ctctctggct aactagggaa cccactgctt    300
aagcctcaat aaagcttgcc ttgagtgctt caagtagtgt gtgcccgtct gttgtgtgac    360
tctggtaact agagatccct cagacccttt tagtcagtgt ggaaaatctc tagcagtggc    420
gcccgaacag ggacttgaaa gcgaaaggga accagagga gctctctcga cgcaggactc    480
ggcttgctga agcgcgcacg gcaagaggcg aggggcggcg actggtgagt acgccaaaaa    540
ttttgactag cggaggctag aaggagagag atgggtgcga gagcgtcagt attaagcggg    600
ggagaattag atcgcgatgg gaaaaaattc ggttaaggcc agggggaaag aaaaaatata    660
aattaaaaca tatagtatgg gcaagcaggg agctagaacg attcgcagtt aatcctggcc    720
tgttagaaac atcagaaggc tgtagacaaa tactgggaca gctacaacca tcccttcaga    780
caggatcaga agaacttaga tcattatata atacagtagc aaccctctat tgtgtgcatc    840
aaaggataga gataaaagac accaaggaag ctttagacaa gatagaggaa gagcaaaaca    900
aaagtaagac caccgcacag caagcggccg ctgatcttca gacctggagg aggagatatg    960
agggacaatt ggagaagtga attatataaa tataaagtag taaaaattga accattagga   1020
gtagcaccca ccaaggcaaa gagaagagtg gtgcagagag aaaaaagagc agtgggaata   1080
ggagctttgt tccttgggtt cttgggagca gcaggaagca ctatgggcgc agcgtcaatg   1140
acgctgacgg tacaggccag acaattattg tctggtatag tgcagcagca gaacaatttg   1200
ctgagggcta ttgaggcgca acagcatctg ttgcaactca cagtctgggg catcaagcag   1260
ctccaggcaa gaatcctggc tgtggaaaga tacctaaagg atcaacagct cctggggatt   1320
tggggttgct ctggaaaact catttgcacc actgctgtgc cttggaatgc tagttggagt   1380
aataaatctc tggaacagat ttggaatcac acgacctgga tggagtggga cagagaaatt   1440
aacaattaca caagcttaat acactcctta attgaagaat cgcaaaacca gcaagaaaag   1500
aatgaacaag aattattgga attagataaa tgggcaagtt tgtggaattg gtttaacata   1560
acaaattggc tgtggtatat aaaattattc ataatgatag taggaggctt ggtaggttta   1620
agaatagttt ttgctgtact ttctatagtg aatagagtta ggcagggata ttcaccatta   1680
tcgtttcaga cccacctccc aaccccgagg ggacccgaca ggcccgaagg aatagaagaa   1740
gaaggtggag agagagacag agacagatcc attcgattag tgaacggatc tcgacggtat   1800
cggttaactt ttaaaagaaa agggggggatt gggggggtaca gtgcagggga aagaatagta   1860
gacataatag caacagacat acaaactaaa gaattacaaa aacaaattac aaaaattcaa   1920
aattttatcg atcacgagac tagcctcgag ggaatgaaag accccacctg taggttttggc   1980 aagctagctt aagtaacgcc attttgcaag gcatggaaaa tacataactg agaatagaga   2040
agttcagatc aaggttagga acagagagac agcagaatat gggccaaaca ggatatctgt   2100
ggtaagcagt tcctgccccg gctcaggggcc aagaacagat ggtccccaga tgcggtcccg   2160
ccctcagcag tttctagaga accatcagat gtttccaggg tgccccaagg acctgaaatg   2220
accctgtgcc ttatttgaac taaccaatca gttcgcttct cgcttctgtt cgcgcgcttc   2280
tgctccccga gctcaataaa agagcccaca accctcact cggcgcgcca gtccggatcc   2340
gccaccatgg aaacactgct gggcctgctg atcctgtggc tgcagctgca gtgggtgtcc   2400
agcaagcagg aagtgaccca gatccctgcc gccctgtctg tgcctgaggg cgagaacctg   2460
gtgctgaact gcagcttcac cgacagcgcc atctacaacc tgcagtggtt cagacaggac   2520
cccggcaagg gcctgacaag cctgctgctg attcagcagc gccagagaga gcagaccagc   2580
```

```
ggcagactga acgccagcct ggataagagc agcggccggt ccaccctgta tatcgccgct    2640
tctcagcctg gcgactccgc cacatatctg tgtgctgtgc ggcctctgta cggcggcagc    2700
tacatcccta ccttcggcag aggcaccagc ctgatcgtgc acccctacat ccagaacccc    2760
gaccccgccg tgtaccagct gagagacagc aagtccagcg acaagagcgt gtgcctgttc    2820
accgacttcg acagccagac caacgtgtcc cagagcaagg acagcgacgt gtacatcacc    2880
gacaagaccg tgctggacat gcggagcatg gacttcaaga gcaacagcgc cgtggcctgg    2940
tccaacaaga gcgatttcgc ctgcgccaac gccttcaaca acagcattat ccccgaggac    3000
acattcttcc caagcccga gagcagctgc gacgtgaagc tggtggaaaa gagcttcgag    3060
acagacacca acctgaactt ccagaacctg agcgtgatcg gcttccggat tctgctgctg    3120
aaggtggccg gcttcaacct gctgatgacc ctgagactgt ggtccagccg gccaagaga    3180
tctggcagcg gcgccaccaa tttcagcctg ctgaaacagg ccggcgacgt ggaagagaac    3240
cctggcccta tgagcatcgg cctgctgtgt tgtgccgctc tgtccctgct gtgggccgga    3300
cctgtgaatg ctggcgtgac acagaccccc aagttccagg tgctgaaaac cggccagagc    3360
atgaccctgc agtgcgccca ggacatgaac cacgagtaca tgagctggta tcggcaggac    3420
cctggcatgg gactgcggct gatccactac tctgtgggcg ccggcatcac cgatcagggc    3480
gaggtgccca acggctacaa tgtgtccaga tccaccaccg aggacttccc actgagactg    3540
ctgtctgccg ccctagcca gacctccgtg tacttctgtg ccagcagcta cgtgggcaac    3600
accggcgagc tgttctttgg cgagggcagc agactgacag tgctggaaga tctgaagaac    3660
gtgttccccc cagaggtggc cgtgttcgag ccttctgagg ccgagatcag ccacacccag    3720
aaagccaccc tcgtgtgtct ggccaccggc ttctacccg accacgtgga actgtcttgg    3780
tgggtcaacg gcaaagaggt gcacagcggc gtgtccaccg atccccagcc tctgaaagag    3840
cagcccgccc tgaacgacag ccggtactgt ctgtcctccc ggctgagagt gtccgccacc    3900
ttctggcaga accccggaa ccacttcaga tgccaggtgc agttctacgg cctgagcgag    3960
aacgacgagt ggacccagga cagagccaag cccgtgactc agatcgtgtc tgccgaggcc    4020
tggggcagag ccgattgtgg ctttaccagc gagagctacc agcagggcgt gctgagcgcc    4080
accatcctgt acgagatcct gctgggcaag gccaccctgt acgccgtgct ggtgtccgcc    4140
ctggtgctga tggccatggt caaacggaag gacttcagag ccaagcgggg aaagcctatc    4200
cctaatcctc tgctgggact ggactccacc ggctctggcg agggcagagg ctctctgctg    4260
acctgcggag atgtgaaaga aaatcccggc cctatgccca ccctgctgcg ggtgtacatc    4320
gacggccccc acggcatggg caagaccacc accacacagc tgctggtggc cctgggcagc    4380
agggacgaca tcgtgtacgt gcccgagccc atgacatact ggcgggtgct gggcgccagc    4440
gagacaatcg ccaacatcta caccacccag cacagactgg accagggcga gatttctgcc    4500
ggcgacgccg ccgtggtcat gaccagcgcc cagatcacca tgggaatgcc ctacgccgtg    4560
acagatgccg tgctggcccc tcacattggc ggcgaggccg atcttctca tgccccaccc    4620
cctgctctga ccatcttcct ggaccggcac cctatcgcct tcatgctgtg ctaccctgcc    4680
gccagatacc tgatgggcag catgacccca caggctgtgc tggctttcgt ggccctgatc    4740
cctcctaccc tgcccggcac caatatcgtg ctgggggccc tgcccgagga cagacacatc    4800
gaccggctgg ccaagagaca gcggcctggc gagagactgg atctggccat gctggccgcc    4860
atcagaagag tgtacggcct gctggccaac accgtgcggg atctgcagtg cggcggctct    4920
tggagagagg actggggcca gctgtctgga acagctgtgc cacctcaagg cgccgagcct    4980
```

```
cagtctaatg ccggccctag accccacatc ggcgacaccc tgtttaccct gttcagagcc    5040
cccgagctgc tggcccccaa cggcgacctg tacaacgtgt tcgcctgggc tctggatgtg    5100
ctggccaagc ggctgcggag catgcacgtg ttcatcctgg actacgacca gagccctgcc    5160
ggctgtagag atgccctgct gcagctgacc agcggcatgg tgcagaccca cgtgaccacc    5220
cctggcagca tccccaccat ctgcgacctg ccccggacct tgccagagat gggcgag      5280 gccaactgag tcgacaatca acctctggat tacaaaattt gtgaaagatt gactggtatt    5340
cttaactatg ttgctccttt tacgctatgt ggatacgctg ctttaatgcc tttgtatcat    5400
gctattgctt cccgtatggc tttcattttc tcctccttgt ataaatcctg gttgctgtct    5460
ctttatgagg agttgtggcc cgttgtcagg caacgtggcg tggtgtgcac tgtgtttgct    5520
gacgcaaccc ccactggttg gggcattgcc accacctgtc agctccttc cgggactttc     5580 gctttccccc tccctattgc cacggcggaa ctcatcgccg cctgccttgc ccgctgctgg    5640 acagggctc ggctgttggg cactgacaat tccgtggtgt tgtcggggaa gctgacgtcc     5700
tttccatggc tgctcgcctg tgttgccacc tggattctgc gcgggacgtc cttctgctac    5760
gtcccttcgg ccctcaatcc agcggacctt ccttcccgcg gcctgctgcc ggctctgcgg    5820
cctcttccgc gtcttcgcct tcgccctcag acgagtcgga tctcccttg ggccgcctcc     5880 ccgcctggaa ttcgagctcg gtacctttaa gaccaatgac ttacaaggca gctgtagatc    5940
ttagccactt tttaaagaa aagggggac tggaagggct aattcactcc caacgaagac      6000
aagatctgct ttttgcttgt actgggtctc tctggttaga ccagatctga gcctgggagc    6060
tctctggcta actagggaac ccactgctta agcctcaata agcttgcct tgagtgcttc     6120 aagtagtgtg tgcccgtctg ttgtgtgact ctggtaacta gagatccctc agacccttt    6180 agtcagtgtg gaaaatctct agcagtagta gttcatgtca tcttattatt cagtatttat    6240
aacttgcaaa gaaatgaata tcagagagtg agggaactt gtttattgca gcttataatg     6300
gttacaaata aagcaatagc atcacaaatt tcacaaataa agcatttttt tcactgcatt    6360
ctagttgtgg tttgtccaaa ctcatcaatg tatcttatca tgtctggctc tagctatccc    6420
gcccctaact ccgcccagtt ccgcccattc tccgccccat ggctgactaa ttttttttat    6480
ttatgcagag gccgaggccg cctcggcctc tgagctattc cagaagtagt gaggaggctt    6540
ttttggaggc ctaggctttt gcgtcgagac gtacccaatt cgccctatag tgagtcgtat    6600
tacgcgcgct cactggccgt cgttttacaa cgtcgtgact gggaaaaccc tggcgttacc    6660
caacttaatc gccttgcagc acatccccct ttcgccagct ggcgtaatag cgaagaggcc    6720
cgcaccgatc gcccttccca acagttgcgc agcctgaatg gcgaatggcg cgacgcgccc    6780
tgtagcggcg cattaagcgc ggcgggtgtg tggttacgc gcagcgtgac cgctacactt     6840
gccagcgccc tagcgcccgc tcctttcgct ttcttccctt cctttctcgc cacgttcgcc    6900
ggctttcccc gtcaagctct aaatcggggg ctccctttag ggttccgatt tagtgcttta    6960
cggcacctcg accccaaaaa acttgattag ggtgatggtt cacgtagtgg gccatcgccc    7020
tgatagacgg ttttcgccc tttgacgttg gagtccacgt tctttaatag tggactcttg     7080
ttccaaactg gaacaacact caaccctatc tcggtctatt cttttgattt ataagggatt    7140
ttgccgattt cggcctattg gttaaaaaat gagctgattt aacaaaaatt taacgcgaat    7200
tttaacaaaa tattaacgtt tacaattttc caggtggcac ttttcgggga aatgtgcgcg    7260
gaacccctat ttgtttattt ttctaaatac attcaaatat gtatccgctc atgagacaat    7320
aaccctgata aatgcttcaa taatattgaa aaaggaagag tatgagtatt caacatttcc    7380
```

```
gtgtcgccct tattcccttt tttgcggcat tttgccttcc tgttttttgct cacccagaaa    7440 cgctggtgaa agtaaaagat gctgaagatc agttgggtgc acgagtgggt tacatcgaac    7500
tggatctcaa cagcggtaag atccttgaga gttttcgccc cgaagaacgt tttccaatga    7560
tgagcacttt taaagttctg ctatgtggcg cggtattatc ccgtattgac gccgggcaag    7620
agcaactcgg tcgccgcata cactattctc agaatgactt ggttgagtac tcaccagtca    7680
cagaaaagca tcttacggat ggcatgacag taagagaatt atgcagtgct gccataacca    7740
tgagtgataa cactgcggcc aacttacttc tgacaacgat cggaggaccg aaggagctaa    7800
ccgctttttt gcacaacatg ggggatcatg taactcgcct tgatcgttgg gaaccggagc    7860
tgaatgaagc cataccaaac gacgagcgtg acaccacgat gcctgtagca atggcaacaa    7920
cgttgcgcaa actattaact ggcgaactac ttactctagc ttcccggcaa caattaatag    7980
actggatgga ggcggataaa gttgcaggac cacttctgcg ctcggccctt ccggctggct    8040
ggtttattgc tgataaatct ggagccggtg agcgtgggtc tcgcggtatc attgcagcac    8100
tggggccaga tggtaagccc tcccgtatcg tagttatcta cacgacgggg agtcaggcaa    8160
ctatggatga acgaaataga cagatcgctg agataggtgc ctcactgatt aagcattggt    8220
aactgtcaga ccaagtttac tcatatatac tttagattga tttaaaactt cattttaat    8280 ttaaaggat ctaggtgaag atcctttttg ataatctcat gaccaaaatc ccttaacgtg    8340
agttttcgtt ccactgagcg tcagaccccg tagaaaagat caaaggatct tcttgagatc    8400
ctttttttct gcgcgtaatc tgctgcttgc aaacaaaaaa accaccgcta ccagcggtgg    8460
tttgtttgcc ggatcaagag ctaccaactc tttttccgaa ggtaactggc ttcagcagag    8520
cgcagatacc aaatactgtc cttctagtgt agccgtagtt aggccaccac ttcaagaact    8580
ctgtagcacc gcctacatac ctcgctctgc taatcctgtt accagtggct gctgccagtg    8640
gcgataagtc gtgtcttacc gggttggact caagacgata gttaccggat aaggcgcagc    8700
ggtcgggctg aacggggggt tcgtgcacac agcccagctt ggagcgaacg acctacaccg    8760
aactgagata cctacagcgt gagctatgag aaagcgccac gcttcccgaa gggagaaagg    8820
cggacaggta tccggtaagc ggcagggtcg gaacaggaga gcgcacgagg gagcttccag    8880
ggggaaacgc ctggtatctt tatagtcctg tcgggtttcg ccacctctga cttgagcgtc    8940
gatttttgtg atgctcgtca ggggggcgga gcctatggaa aaacgccagc aacgcggcct    9000
ttttacggtt cctggccttt tgctggcctt ttgctcacat gttctttcct gcgttatccc    9060
ctgattctgt ggataaccgt attaccgcct ttgagtgagc tgataccgct cgccgcagcc    9120
gaacgaccga gcgcagcgag tcagtgagcg aggaagcgga agagcgccca atacgcaaac    9180
cgcctctccc cgcgcgttgg ccgattcatt aatgcagctg gcacgacagg tttcccgact    9240
ggaaagcggg cagtgagcgc aacgcaatta atgtgagtta gctcactcat taggcacccc    9300
aggctttaca ctttatgctt ccggctcgta tgttgtgtgg aattgtgagc ggataacaat    9360
ttcacacagg aaacagctat gaccatgatt acgccaagcg cgcaattaac cctcactaaa    9420
gggaacaaaa gctggagctg ca                                              9442
```

<210> SEQ ID NO 6
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Ser Leu Leu Met Trp Ile Thr Gln Cys
1               5

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aagtagtgtg tgcccgtctg                                                    20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cctctggttt ccctttcgct                                                    20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cagggtctgg gagccaagt                                                     19

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcacagtgct ggacattgac a                                                  21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
cccaccgaac ccaagaaact a                                                  21
```

US 10,201,597 B2

CODON-OPTIMIZED LENTIVIRAL VECTOR FOR STEM CELL REPROGRAMMING

CROSS REFERENCE TO RELATED APPLICATIONS

This application claims the benefit under 35 U.S.C. Section 119(e) of U.S. Provisional Patent Application Ser. No. 62/057,397, entitled "CODON-OPTIMIZED LENTIVIRAL VECTOR FOR STEM CELL REPROGRAMMING" filed Sep. 30, 2014, the contents of which are incorporated herein by reference.

SEQUENCE LISTING

The instant application contains a Sequence Listing which has been submitted electronically in ASCII format and is hereby incorporated by reference in its entirety. Said ASCII copy, created on Sep. 23, 2015, is named 30435.274-WO-U2_SL.txt and is 22,038 bytes in size.

TECHNICAL FIELD

This invention relates generally to the fields of immunology and gene delivery, and in particular, gene transfer vectors and genetically modified stem cells.

BACKGROUND OF THE INVENTION

The immune system protects the human body against infection as well as diseases such as cancer. An important aspect of the immune system is the adaptive immune response. The adaptive immune response is antigen-specific and allows for a targeted response against a specific pathogen or diseased cell. T cells play an essential role in this response due to their ability to recognize specific antigens through T cell receptors (TCR). The specificity of a T cell depends on the sequence of its TCR.

There is significant interest in genetically engineering T cells in order to target cancer cells. In one strategy, T cells are transduced with viral vectors encoding T cell receptors that recognize cancer-specific antigens. However, such immunotherapy techniques require the extraction, processing, and reintroduction of T cells from a patient's own blood, making the procedure time-consuming and expensive. In addition, because there are many circumstances where patients have very little of their own T cells available to be reprogrammed (e.g. patients with HIV infections), not all patients can benefit from such treatments.

There have been a number of efforts directed towards mass production of reprogrammed T cells using stem cell technology. For example, the generation of tumor-specific T cells from genetically modified hematopoietic stem cells obtained from the fetal liver or cord blood has been reported (see, e.g. Vatakis, et al. *Proceedings of the National Academy of Sciences* 2011, 108(51): E1408-E1416; Giannoni et al. *Molecular Therapy* 2013, 21(5): 1044-1054). In another study, retroviral vectors have been used to genetically program bone marrow cells for TCR engineering in mouse models (see, e.g. Yang, et al. *Proceedings of the National Academy of Sciences of the United States of America* 2005, 102(12): 4518-4523).

Because of the significant potential impact related to the utilization of antigen-specific T cells in treating tumors and cancer cells, there is a need for compositions and techniques that enable the mass production of T cells having defined antigen specificity. This invention addresses this and other needs in the art.

SUMMARY OF THE INVENTION

The present invention provides method and materials for programming stem cells in order to form cytotoxic T cells that can target and kill cancer cells. Illustrative embodiments of the invention include transducing peripheral blood stem cells (PBSCs) with a vector comprising codon-optimized polynucleotides encoding TCR alpha and beta chain polypeptides. Working embodiments of the invention disclosed include PBSCs transduced with a lentiviral vector that comprises a codon optimized TCR specific for the cancer-testis antigen NY ESO-1. These gene-modified cells may be used, for example, in a hematopoietic stem cell transplantation setting to treat patients with NY ESO-1 positive cancers.

The invention disclosed herein has a number of aspects. One aspect of the present invention is a composition of matter comprising a codon optimized polynucleotide having a sequence shown in SEQ ID NO: 1 (encoding a TCR alpha chain polypeptide shown in SEQ ID NO: 2). In certain embodiments, the composition of matter alternatively or further comprises a polynucleotide having a codon-optimized sequence shown in SEQ ID NO: 3 (encoding a TCR beta chain polypeptide shown in SEQ ID NO: 4). In typical embodiments of the present invention, the polynucleotide having the sequence shown in SEQ ID NO: 1 and the polynucleotide having the sequence shown in SEQ ID NO: 3 are disposed within a vector adapted to express a functional T cell receptor (TCR) comprising a TCR alpha chain polypeptide shown in SEQ ID NO: 2 and a TCR beta chain polypeptide shown in SEQ ID NO: 4. In certain embodiments, the vector further comprises additional functional elements such as one or more of a PET reporter, a suicide gene, a murine stem cell virus (MSCV) promoter, a 3' self-inactivating (SIN) LTR, a central polypurine tract (cPPT), a Rev-responsive element (RRE); a 5' LTR, and/or a sr39 thymidine kinase. In an illustrative example, the vector encodes a HSV1-sr39tk thymidine kinase polypeptide.

Embodiments of the invention include host cells transduced with a vector as described herein and methods for using such cells. Embodiments of the invention include methods of inhibiting the growth of target cancer cells expressing NY ESO-1 antigen. Typically, such methods comprise the steps of combining the target cells with peripheral blood stem cells (PBSC) transduced with a vector designed to express a functional T cell receptor (TCR) alpha chain polypeptide as shown in SEQ ID NO: 2 and encoded by a polynucleotide having a sequence shown in SEQ ID NO: 1 and a TCR beta chain polypeptide as shown in SEQ ID NO: 4 and encoded by a polynucleotide having a sequence shown in SEQ ID NO: 3. In such methods, the target cell and the PBSC are combined under conditions selected to allow the PBSC to recognize the target cell using the TCR alpha chain polypeptide shown in SEQ ID NO: 2 and the TCR beta chain polypeptide shown in SEQ ID NO: 4, and inhibit growth of cancer cells expressing the NY ESO-1 antigen.

In one or more embodiments of the invention, the target cell and the PBSC are combined in vivo. For example, the target cell and the PBSC may be combined in an individual diagnosed with a pathological condition such as cancer. In these methods, the target cell is typically a cancerous human cancer cell that expresses the NY ESO-1 antigen, such as a melanoma cell. In one embodiment of the invention, the individual diagnosed with a pathological condition has received chemotherapy or radiation therapy prior to combining the target cell with the PBSC. In some embodiments of the invention, the individual has received a myelodepleting chemotherapy regimen prior to combining the target cell with the PBSC. In certain embodiments, the method can comprise the step of combining the genetically modified PBSC with a positron emission tomography tracer.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

FIG. 3 illustrates sr39tk functionality using a NY ESO-1 TCR/TK lentiviral vector.

FIG. 5 illustrates an experimental system to test ESO/TK PET reporter and suicide gene function in vivo, in accordance with one embodiment of the present invention. (5A) Schematic of lentiviral vector used to engineer HSCs to express the ESO/TK transgene. (5B) CD34 enriched G-CSF mobilized peripheral blood stem cells from healthy donors were stimulated overnight then transduced with a lentivirus encoding the ESO/TK vector. The next day, cells were transplanted to irradiated NSG-A2.1 neonates by intrahepatic injection. Two months post-transplant, peripheral blood was screened for human chimerism and lymphoid development by flow cytometry. (5C) Cells were first gated on the characteristic lymphocyte SSC×FSC profile, followed by examination of murine and human CD45 to exclude non-nucleated cells. Human CD45+ cells were examined for hCD19 to identify B- and hCD3 to identify T-lineage cells. T-cells were gated into separate hCD4 helper and hCD8 effector subsets, and evaluated for their ability to bind the NY-ESO-1 tetramer as indicative of TCR expression.

FIG. 6 shows graphs illustrating the development of human cells in NSG-A2.1 mice transplanted with PBSCs. Non-transduced and ESO/TK transduced PBSC transplanted humanized mouse peripheral blood was assayed by flow cytometry at 2 months post-transplant. No significant difference was observed in proportions of (6A) human chimerism, (6B) B-cells, (6C) T-cells, (6D) the CD4 subset, (6E) or the CD8 subset of T-cells. (6F) NY-ESO-1-TCR bearing CD4 cells were not observed. (6G) NY-ESO-1-TCR bearing CD8 T-cells developed only in the ESO/TK cohort.

FIG. 7 shows graphs illustrating the effector function of in vivo derived NY-ESO-1-TCR bearing cells from HSCs. Ex vivo expanded splenocytes from ESO/TK humanized mice were evaluated alongside ESO/TK transduced or mock transduced normal donor PBMCs. 51Cr release assays were performed on (7A,7B) splenocytes from ESO/TK humanized mice (ms1 and ms2), (7C) healthy donor ESO/TK transduced T-cells, and (7D) mock transduced T-cells cocultured with HLA mismatched (M257) or HLA matched (M257/A2.1 and M407) melanoma cell lines. (7E) IFNγ ELISA was performed to validate results from cytotoxicity assays.

FIG. 8 illustrates high-resolution sr39TK PET reporter imaging of gene-modified cells in vivo. (8A) Experimental procedure for PET imaging. Mice were injected with 250 uCi [$^{18}$F]-FHBG and PET/CT imaged. Scans of (8B) non-transplanted NSG-A2.1, (8C) non-transduced humanized, and (8D) ESO/TK-transduced humanized mice. Probe was detected in the gastrointestinal tract and gall bladder in all mice. In ESO/TK-transduced humanized mice, signal was detectable in the long bones of the arms and legs, the sternum, the thymus, and vertebrae.

FIG. 9 illustrates how GCV ablates gene modified cells hematopoietic niches. Mice were PET/CT scanned with [$^{18}$F]-FHBG before and 7 d after treatment with (9A) vehicle or (9B) GCV. Three of five representative vehicle treated mice and five of five GCV treated mice are shown. Neutral density masks were drawn to visually mute background GB and GI signal. ROIs were drawn on femurs, humeri, and the thymus of each mouse in pre- and post-treatment scans. (9C) ESO/TK mice treated with vehicle showed no significant difference between pre- and post-treatment scans (P=0.402). (9D) There was a significant decrease in [$^{18}$F]-FHBG PET signal in hematopoietic ROIs in ESO/TK mice treated with GCV (P<0.001).

FIG. 10 shows graphs illustrating immunophenotyping and VCN analysis after drug treatment. Harvested splenocytes from non-transduced humanized, vehicle treated ESO/TK-transduced humanized, and GCV treated ESO/TK-transduced humanized mice were evaluated by flow cytometry. No significant difference was observed for (10A) human chimerism, (10B) human B-cell or (10C) T-cell composition. (10D) A significant decrease of CD8+NY-ESO-1-TCR+ cells was observed after GCV treatment in the ESO/TK group (P=0.006). (10E-G) VCN analysis of gDNA harvested from the sternum, thymus, femurs, humeri, and spleen were measured for each treatment group.

FIG. 12 illustrates ROI analysis. (12A) Schematic of ROIs drawn on PET imaged mice. 3 d cylindrical or spherical ROIs were drawn using Amide software on hematopoietic niches to determine probe uptake and arm muscle for background subtraction. (12B) There was significant [$^{18}$F]-FHBG uptake in the hematopoietic niches of ESO/TK mice compared with mock transduced controls. (12C) [$^{18}$F]-FHBG uptake in non-transduced humanized mice before and after GCV treatment.

FIG. 13 illustrates chimerism, vector marking, and PET probe signal in vertebrae. (13A) Cells harvested from individual vertebrae were evaluated for human chimerism by flow cytometry and vector marking by qPCR. (13B) Data were matched with [$^{18}$F]-FHBG PET scan.

DETAILED DESCRIPTION OF THE INVENTION

Figure 1:
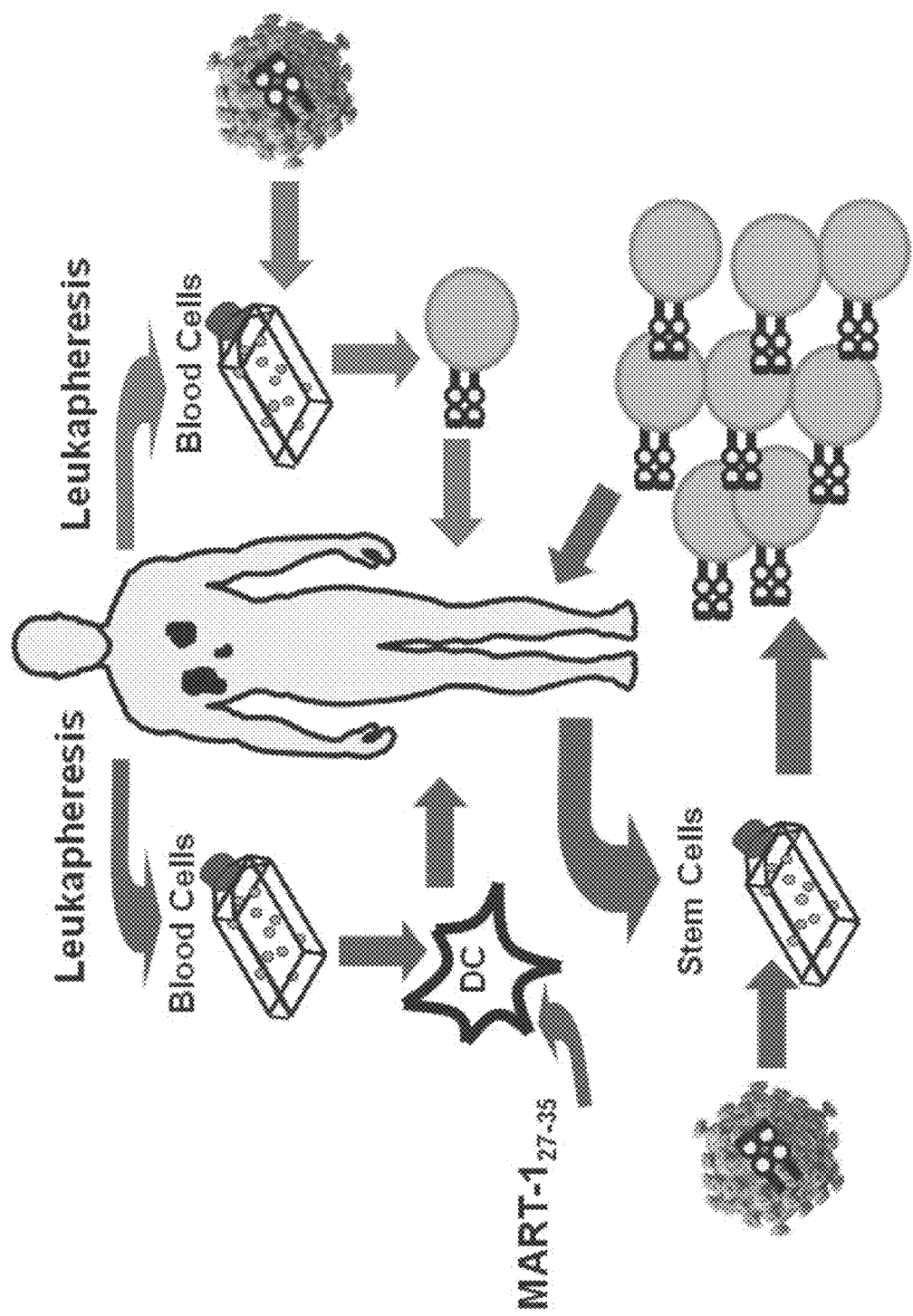
FIG. 1 illustrates a process for the regeneration of an immune system using TCR engineered hematopoietic stem cells, in accordance with one embodiment of the present invention.
Figures 2A, 2B:
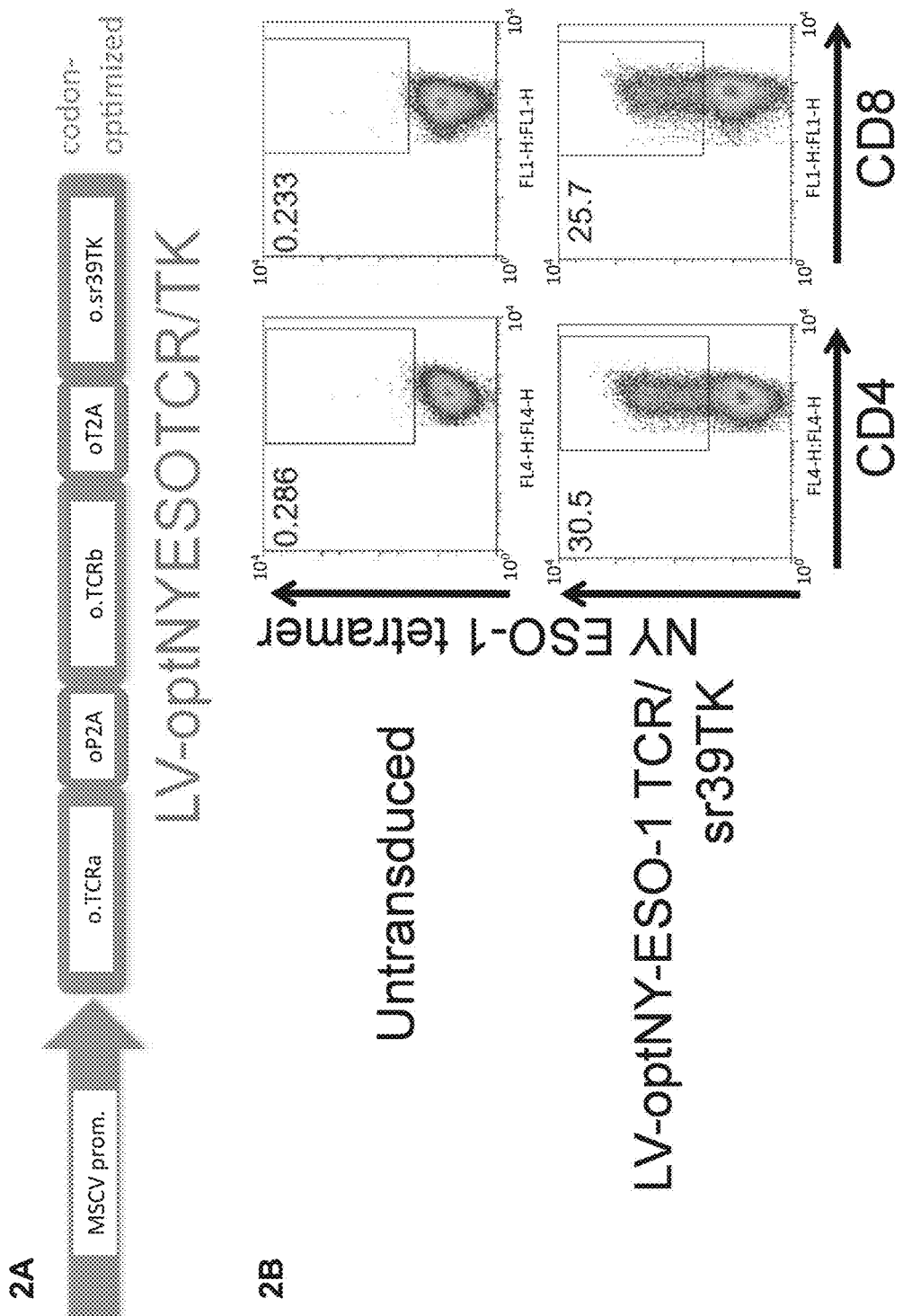
FIG. 2 illustrates TCR expression and functionality using a NY ESO-1 TCR/TK lentiviral vector.
Figure 2C:
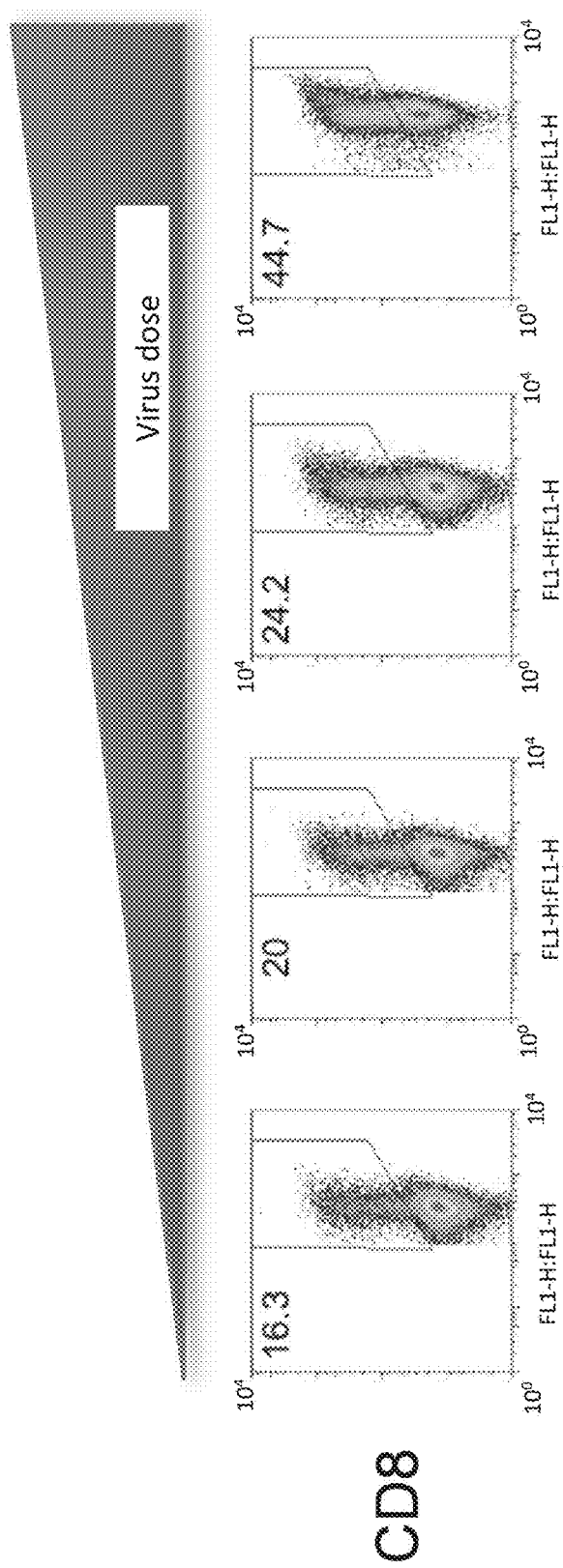
Figure 2D:
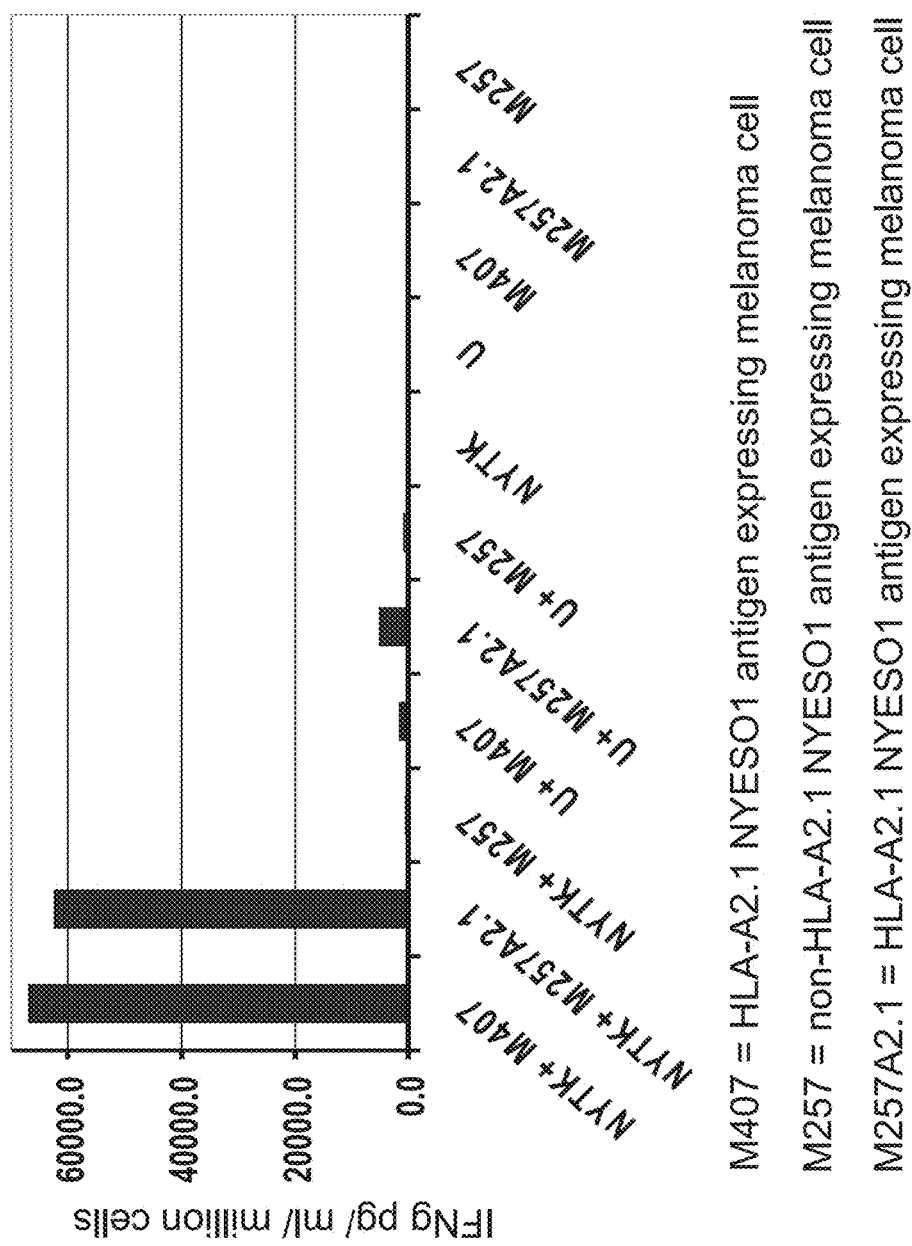
Figure 4:
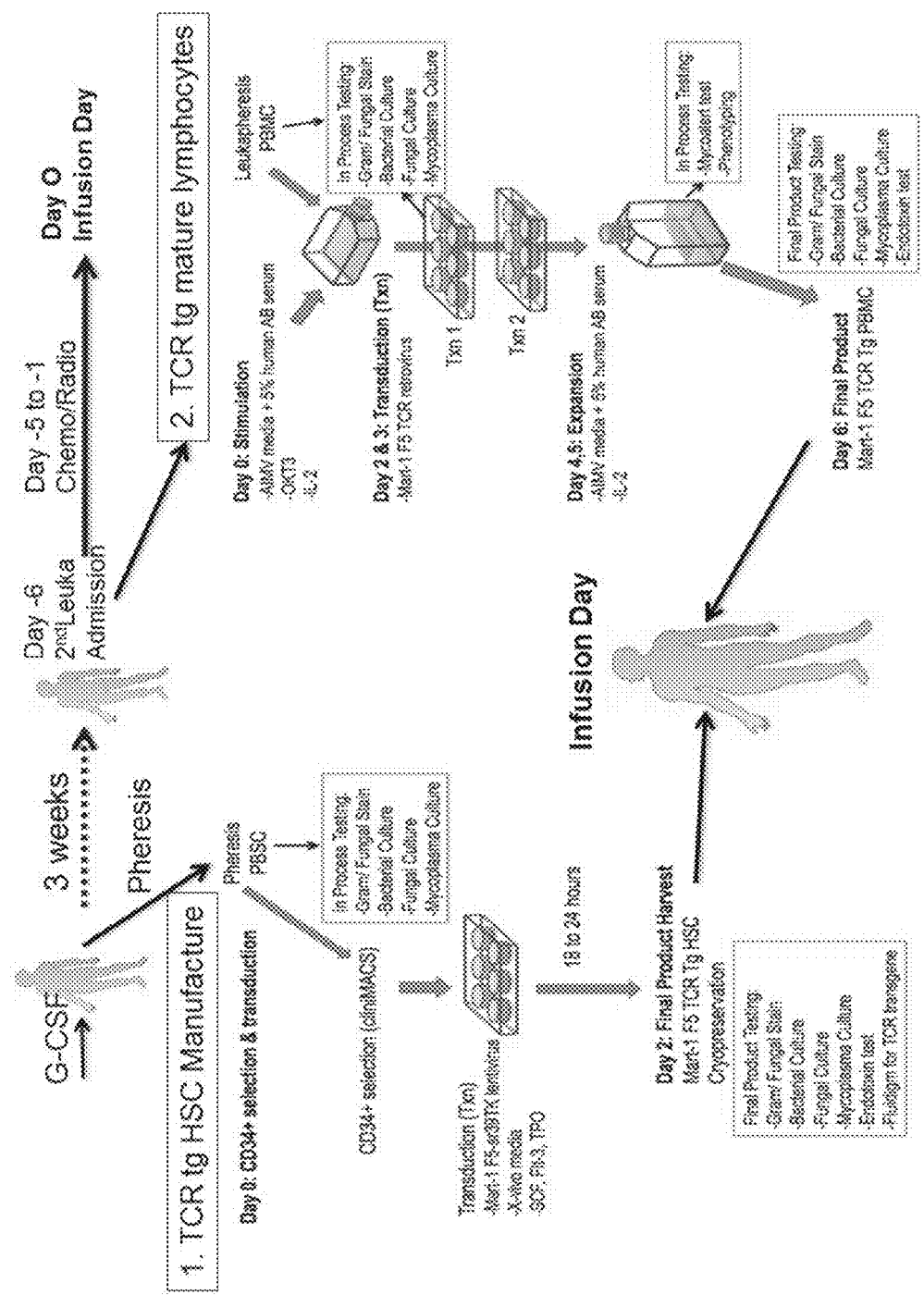
FIG. 4 illustrates a process for administering NY ESO-1 TCR/sr39tk-modified PBSC in patients, in accordance with one embodiment of the present invention.

Many of the techniques and procedures described or referenced herein are well understood and commonly employed using conventional methodology by those skilled in the art. In the description of the preferred embodiment, reference is made to the accompanying drawings, which form a part hereof, and in which is shown by way of illustration a specific embodiment in which the invention may be practiced. It is to be understood that other embodiments may be utilized and structural changes may be made without departing from the scope of the present invention.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

The term "gene delivery" or "gene transfer" refers to methods or systems for inserting foreign DNA into target cells. Virus mediated gene delivery utilizes the ability of a virus to inject its DNA inside a host cell.

The term "retrovirus" refers to a single-stranded RNA virus that replicates in a host cell through the process of reverse transcription. Once inside the host cell, the retrovirus utilizes reverse transcriptase to convert its genomic RNA into double-stranded DNA. This double-stranded DNA form of the virus is then incorporated into the genome of the infected host cell, at which point it is referred to as a "provirus." The host cell treats the provirus as part of its own genome, translating and transcribing the viral genes along with the cell's own genes.

The term "transduction" refers to the delivery of a gene using a lentiviral or retroviral vector by means of viral infection rather than by transfection. In certain embodiments, retroviral transduction is carried out by packaging the vectors into virions prior to contact with a cell.

The term "vector" refers to a nucleic acid molecule used as a vehicle for transporting foreign genetic material into another cell, where it can be replicated and/or expressed. In the present specification, "plasmid" and "vector" are used interchangeably, as a plasmid is a commonly used form of vector. Moreover, the invention is intended to include other vectors which serve equivalent functions.

The term "expression vector" includes any vector (e.g., a plasmid, cosmid or phage chromosome) containing a gene construct in a form suitable for protein expression by a cell.

The term "retroviral vector" refers to a vector containing structural and functional genetic elements that are primarily derived from a retrovirus.

The term "lentiviral vector" refers to a vector containing structural and functional genetic elements outside the LTRs that are primarily derived from a lentivirus. Lentiviruses are a subclass of retroviruses. They have been adapted as gene delivery vehicles (vectors) due to their ability to integrate into the genome of non-dividing cells, which is a unique feature of lentiviruses, since other retroviruses can only infect dividing cells.

The term "promoter" refers to a region of DNA that initiates transcription of a particular gene.

The term "long terminal repeat (LTR)" refers to domains of base pairs located at the ends of retroviral DNAs that repeat hundreds or thousands or times. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals and sequences needed for replication and integration of the viral genome. The LTR, segmented into the U3, R, and U5 regions, appears at both the 5' and 3' ends of the viral genome.

The term "self-inactivating" or "SIN," refers to a vector in which the right (3') LTR enhancer-promoter region (i.e. U3 region) has been modified (e.g., by deletion or substitution) to prevent viral transcription beyond the first round of viral replication. Consequently, the vector is capable of infecting and then integrating into the host genome only once, and cannot be passed further, thereby increasing the safety of the use of the vector as a gene delivery vector.

The term "suicide gene" refers to a gene that expresses a product that is fatal to the cell expressing the suicide gene. Activation of the suicide gene causes the cell to kill itself through apoptosis.

The term "stem cell" refers to undifferentiated biological cells that have the ability to divide and create identical copies of themselves or differentiate into specialized cells. Hematopoietic stem cells (HSCs) are able to differentiate into specialized blood cells, such as T cells. HSCs are found in the bone marrow of adults and, in small numbers, in peripheral blood.

TYPICAL EMBODIMENTS OF THE INVENTION

The present invention provides method and materials for programming stem cells in order to form cytotoxic T cells that can target and kill cancer cells. Illustrative embodiments of the invention include transducing peripheral blood stem cells (PBSCs) with a vector comprising codon-optimized polynucleotides encoding TCR alpha and beta chain polypeptides.

Working embodiments of the invention disclosed include PBSCs transduced with a lentiviral vector that comprises a codon optimized TCR specific for the cancer-testis (CT) antigen NY ESO-1. Cancer-testis antigens are expressed in a variety of cancers, but not in normal adult tissues, except for germ cells of the testis. Thus, there is significant interest in utilizing CT antigens as targets for immunotherapy. In particular, NY-ESO-1 has been a target of interest for antigen-specific immunotherapy (see, e.g. U.S. Pat. No. 8,519,106). For example, the use of the NY ESO-1 TCR without codon optimization and vehiculized by a retroviral vector has been reported (see, e.g. Robbins, et al. *Journal of Clinical Oncology* 2011, 29(7): 917-924). Further information regarding NY-ESO-1 (e.g. nucleotide and amino acid sequences, origin) may be found in the UniProtKB/Swiss-Prot database hosted by EMBL under primary accession number P78358.

The invention disclosed herein has a number of aspects and embodiments. For example, one aspect of the present invention is a composition of matter comprising a polynucleotide having a sequence shown in SEQ ID NO: 1 (encoding the TCR alpha chain). In certain embodiments, the composition of matter further comprises a polynucleotide having a sequence shown in SEQ ID NO: 3 (encoding the TCR beta chain). In embodiments of the invention, both SEQ ID NO: 1 and SEQ ID NO: 3 are a codon optimized polynucleotides. Codon optimization is a technique for maximizing protein expression by increasing the translation efficiency of the gene of interest. This can be accomplished by replacing wild-type DNA sequences with more highly expressed species-dependent sequences. Codons with higher frequency of occurrence are used to maximize or increase the level of protein expression. In the present invention, the use of codon-optimized sequences allows for the more efficient production of the TCR alpha and beta chains in human cells.

In typical embodiments of the invention, a polynucleotide having the sequence shown in SEQ ID NO: 1 and a polynucleotide having the sequence shown in SEQ ID NO: 3 are disposed within a vector adapted to express in mammalian cells a functional T cell receptor (TCR) comprising a TCR alpha chain receptor polypeptide shown in SEQ ID NO: 2 and a TCR beta chain polypeptide shown in SEQ ID NO: 4. In an exemplary implementation, the vector comprises a polynucleotide encoding a T cell receptor (TCR) alpha chain comprising nucleotide 2347 to nucleotide 3168 of SEQ ID NO: 5 and a polynucleotide encoding a T cell receptor (TCR) beta chain comprising nucleotide 3250 to nucleotide 4174 of SEQ ID NO: 5.

In one or more embodiments of the invention, the vector is a lentiviral vector. In certain embodiments, the vector is a lentiviral vector and further comprises a PET reporter and/or a suicide gene. Positron emission tomography (PET) and single photon emission tomography (SPECT) are highly sensitive imaging techniques for imaging radiolabeled markers (see, e.g. Acton, et al. *QJ Nucl Med Mol Imaging* 2005, 49: 349-60). Such imaging techniques may be used in conjunction with the compositions of matter disclosed herein to monitor and track cells, including their function, survival, differentiation status, etc. Reporter genes include receptor-based reporters, such as the dopamine type-2 receptor (D2R), enzyme-based reporters, such as herpes simplex virus type-1 thymidine kinase (HSV1-tk), and transporters, such as sodium-iodide symporter (NIS). For example, in one approach, cells are transfected with a reporter gene, HSV1-tk, whose expression is further visualized using a radioactive PET or SPECT reporter probe.

In a specific embodiment, the vector is a lentiviral vector, LV-optNYESOTCR/TK, that expresses the PET reporter and suicide gene, herpes simplex virus type 1 (HSV1)-sr39tk. Preferably, the HSV1-sr39tk is codon-optimized. The inclusion of the HSV1-sr39tk in the retroviral vector provides various functions. For example, the inclusion of the HSV1-sr39tk gene may be used as a PET reporter gene for the study of hematopoietic and immune reconstitution. Also, the inclusion of the HSV1-sr39tk gene may be used as a suicide gene that allows the depletion of transduced cells if they become toxic. Suicide genes, such as HSV1-tk, provide a method for increasing the safety and reliability of vectors and transduced cells. By incorporating an effective suicide gene (e.g. a herpes simplex virus type-1 thymidine kinase) into a vector, cells expressing the gene can be selectively killed, for example by using an appropriate agent ganciclovir. This is desirable in case the recombinant gene causes a mutation leading to uncontrolled cell growth.

In embodiments of the invention, the retroviral vector can comprise one or more genes and/or regulatory elements such as a PET reporter gene, a suicide gene, a murine stem cell virus (MSCV) promoter, a 3' self-inactivating (SIN) LTR, a central polypurine tract (cPPT), a Rev-responsive element (RRE); a 5' LTR, and/or a sr39 thymidine kinase (sr39tk). In an exemplary implementation, the retroviral vector comprises a PET reporter, a suicide gene, a murine stem cell virus (MSCV) promoter comprising nucleotide 1955 to nucleotide 2329 of SEQ ID NO: 5; a 3' self-inactivating (SIN) LTR comprising nucleotide 5971 to nucleotide 6204 of SEQ ID NO: 5; a central polypurine tract (cPPT) comprising nucleotide 1809 to nucleotide 1926 of SEQ ID NO: 5; a Rev-responsive element (RRE) comprising nucleotide 933 to nucleotide 1790 of SEQ ID NO: 5; a 5' LTR comprising nucleotide 6 to nucleotide 415 of SEQ ID NO: 5; and/or a sr39 thymidine kinase comprising nucleotide 4294 to nucleotide 5289 of SEQ ID NO: 5.

In a further embodiment, the SIN 3' LTR comprises a Delta unique 3' (U3) region comprising nucleotide 5971 to nucleotide 6023 of SEQ ID NO: 5; a redundancy (R) region comprising nucleotide 6024 to nucleotide 6121 of SEQ ID NO: 5; and/or a unique 5' (U5) region comprising nucleotide 6122 to nucleotide 6204 of SEQ ID NO: 5. The 5'LTR comprises a unique 3' (U3) region comprising nucleotide 6 to nucleotide 235 of SEQ ID NO: 5; a redundancy (R) region comprising nucleotide 236 to nucleotide 332 of SEQ ID NO: 5; and a unique 5' (U5) region comprising nucleotide 333 to nucleotide 415 of SEQ ID NO: 5.

In another aspect of the present invention, a host cell transduced with a vector as described herein is disclosed. In one or more preferred embodiments, the host cell is a stem cell. By incorporating TCR genes into stem cells, a renewable source of cancer-fighting lymphocytes may be generated.

Typically, T cells of the present invention are derived from hematopoietic stem cells (HSCs), which are mostly found in the bone marrow. However, HSCs have the ability to migrate through the bone marrow and into the peripheral blood. This process, known as "mobilization," may be amplified by various methods. In one method, a cytokine, such as granulocyte colony stimulating factor (G-CSF), is used to stimulate the bone marrow to produce granulocytes and stem cells and release them into the bloodstream. The use of G-CSF-mobilized PBSCs instead of HSCs obtained from bone marrow allows the compositions of matter and methods disclosed herein to be more broadly applicable since, for example, PBSCs can be harvested from a patient without the use of general anesthesia. Currently, there is no standard stem cell assay which is universally accepted. However, the number of CD34+ cells and quantity of colony-forming unit-granulocyte macrophage (CFU-GM) present in collected peripheral blood are commonly used as indexes of stem cell quantities (see, e.g. Demirer, et al. *Stem Cells* 1996, 14: 106-116).

Methods for obtaining granulocyte-colony stimulating factor (G-CSF)-mobilized peripheral blood stem cell (PBSC) are known in the art and described, for example in publications such as Takeyama et al., Transfus Apher Sci. 2004 December; 31(3):233-43; Zi-Min et al. J Hematol Oncol. 2010; 3: 51; Moon et al, Transfus Apher Sci. 2013 Aug. 24. doi:pii: S1473-0502(13)00279-6; and Fadilah et al., Transfus Apher Sci. 2013 Aug. 22. pii: S1473-0502(13) 00259-0. Peripheral blood stem cells can be readily identified by a number of methods known in the art such as their marker expression profile. In some embodiments of the invention, the peripheral blood stem cells are identified by observing the expression of PB-CD34+ in such cells.

In another aspect of the present invention, the TCR transduced PBSC cells are designed to kill target cells expressing a NY ESO-1 antigen. In a preferred embodiment, PBSC are genetically modified via lentiviral vector as described herein (e.g. LV-optNYESOTCR/TK) to express a cancer-specific TCR targeting the cancer-testis antigen NY ESO-1 and a reporter/suicide gene such as sr39tk PET. These gene-modified cells may be used, for example, in a hematopoietic stem cell transplantation setting to treat patients with NY ESO-1 positive cancers.

Another aspect of the present invention includes methods of inhibiting the growth of a target cell expressing a NY ESO-1 antigen. The method comprises the steps of combining the target cell with a peripheral blood stem cell (PBSC) transduced with a vector comprising a polynucleotide having a sequence shown in SEQ ID NO: 1 and a polynucleotide having a sequence shown in SEQ ID NO: 3. The vector expresses a functional T cell receptor (TCR) alpha chain polypeptide shown in SEQ ID NO: 2 and a TCR beta chain polypeptide shown in SEQ ID NO: 4. The target cell and the PBSC are then combined under conditions selected to allow the PBSC to recognize the target cell using the TCR alpha chain polypeptide shown in SEQ ID NO: 2 and the TCR beta chain polypeptide shown in SEQ ID NO: 4, and inhibit growth of the target cell so that the growth of the target cell expressing the NY ESO-1 antigen is inhibited.

In one or more embodiments of the invention, the target cell and the PBSC are combined in vivo. In one embodiment, the target cell and the PBSC are combined in an individual diagnosed with a pathological condition. In one specific instance, the pathological condition is cancer. In a further embodiment, the target cell is a human cancer cell. Examples of cancer cells include melanoma cells, pancreatic cancer cells, colon cancer cells, ovarian cancer cells, liver cancer cells, lung cancer cells, cervical cancer cells, brain cancer cells, bladder cancer cells, and breast cancer cells. In another embodiment, the individual diagnosed with a pathological condition has received chemotherapy or radiation therapy prior to combining the target cell with the PBSC. In a further embodiment, the individual has received a myelodepleting chemotherapy regimen prior to combining the target cell with the PBSC. In another embodiment, the method further comprises the step of combining the PBSC with a positron emission tomography tracer.

In one exemplary implementation, PBSC is obtained from patients with NY ESO-1 positive cancers that are not responding to standard therapies. The obtained PBSC are genetically modified with LV-optNYESOTCR/TK and administered back to the patients after they have received a myelodepleting conditioning chemotherapy regimen. By engrafting NY ESO-1 TCR/sr39tk-modified PBSC in patients with metastatic cancers who have received a prior chemoradiotherapy conditioning regimen, a skewed production of mature lymphocytes with anti-tumor activity due to their expression of the transgenic TCR occurs.

Experiments have shown that fully functional, clinical-grade genetically modified TCR transgenic lymphocytes may be manufactured at GMP compliance and administered within one week. TCR transgenic adoptive cell transfer has been found to result in high initial anti-tumor regressions. Tumors relapse as TCR transgenic cells decrease in frequency and function in blood. Insertion of TCR genes into HSCs results in the continuous production of fully functional TCR transgenic lymphocytes.

EXAMPLES

Example 1: HSV-sr39TK Positron Emission Tomography and Suicide Gene Elimination of Human Hematopoietic Stem Cells and their Progeny in Humanized Mice Abstract Engineering immunity against cancer by the adoptive transfer of hematopoietic stem cells (HSC) modified to express antigen-specific T-cell-receptors (TCR) or chimeric antigen receptors (CAR) generates a continual supply of effector T-cells, potentially providing superior anti-cancer efficacy compared with the infusion of terminally differentiated T-cells. Here we demonstrate the in vivo generation of functional effector T-cells from CD34-enriched human peripheral blood stem cells (PBSC) modified with a lentiviral vector designed for clinical use encoding a TCR recognizing the cancer/testes antigen NY-ESO-1, co-expressing the PET/suicide gene sr39TK. Ex vivo analysis of T-cells showed antigen- and HLA-restricted effector function against melanoma. Robust engraftment of gene-modified human cells was demonstrated with PET reporter imaging in hematopoietic niches such as femurs, humeri, vertebrae, and the thymus. Safety was demonstrated by the in vivo ablation of PET signal, NY—ESO-1-TCR bearing cells, and integrated lentiviral vector genomes upon treatment with ganciclovir (GCV), but not with vehicle control. Our study provides support for the efficacy and safety of gene-modified HSCs as a therapeutic modality for engineered cancer immunotherapy.

Introduction

The genetic modification of hematopoietic stem cells (HSC) is an attractive approach for the treatment of disease, first demonstrated in primary immune deficiencies (1-3). Transplantation of gene-modified HSCs into patients resulted in long term correction of disease in the majority of subjects, and paved the way for future applications using viral vectors to modify hematopoietic cells (4). Gene therapy has also proven a promising modality for engineered immunity. Preclinical studies and clinical trials that engineered peripheral T-cells with cancer-antigen reactive T-cell-receptors (TCR) and chimeric antigen receptors (CAR) have achieved tumor regression in patients (5-8). Unfortunately, not all patients developed a lasting and complete response with most demonstrating transient anti-tumor reactivity. The observation that many patients initially responded with a reduction in tumor burden yet ultimately relapsed is hypothesized to be due to the nature of the ex vivo T-cell expansion protocol, which pushes T-cells to a differentiation state characterized by robust cytotoxic effector function at the cost of regenerative capacity (9-11). The ability to generate an antigen specific T-cell infusion product with long-lasting in vivo persistence, such as central memory T cells, is an area of active pre-clinical and clinical investigation (12-16).

HSCs represent the most primitive hematopoietic cells with the greatest regenerative potential, and recent preclinical studies have examined the modification of HSCs for cancer immunotherapy. The introduction of a pre-arranged TCR to HSCs was first demonstrated in mice (17), and later in humanized mouse models (18-20). These studies demonstrated that engineered HSCs give rise to progeny T-cells expressing the introduced transgenic TCR, and are reactive against cells expressing the target antigen. CARs have also been shown useful in the modification of HSCs for therapeutic immunotherapy, specifically against CD19 for B-cell malignancies (21). The duration of de novo T-cell production in this chimeric setting is currently unknown, though clinical evidence supports the notion that HSCs support long-lasting thymopoiesis (22, 23).

The use of strong enhancer/promoter sequences within the vector necessary to achieve therapeutic levels of the introduced transgene can result in activation of proto-oncogenes in proximity of the integration site, and clonal expansion culminating in leukemic transformation of modified hematopoietic cells (24). These events, while rare, mandate the incorporation of safety elements in vector design including insulators (25) or internal promoters with self-inactivating long terminal repeats (LTR) lacking strong enhancers (26-28). An additional concern particular to T-cell immunotherapy is that the introduction of a self-antigen-specific TCR or CAR has the potential to induce an auto-immune reaction. There have been several reports of cytokine storm syndrome after the transplant of CAR-transduced T cells (29, 30) which may benefit from an approach to decrease the number of transgenic cells through the use of a suicide gene. Immunotherapy is designed to focus primarily on tumor-specific antigens, though low level of these antigens may be expressed by normal tissue leading to unintended off-target reactivity. In clinical trials targeting melanoma by transfer of T-cells engineered to express a human TCR against the $_{27-35}$MART-1 peptide, acute skin rash and auto-immune vitiligo are often observed due to reaction against normal melanocytes that also express the MART-1 antigen (31). More concerning is the recent report of the death of two patients in a clinical trial using autologous T-cells modified with an affinity-enhanced TCR against the MAGE3 antigen due to unpredicted reactivity to cardiac Titin (32). The possibility of occult cytotoxicity of the TCR or CAR further supports the inclusion of a method to eliminate gene-modified cells in vivo.

Suicide genes can be incorporated as a safety switch to selectively ablate gene-modified cells during an adverse event. These have been demonstrated in the setting of clonal outgrowth from activation of a proto-oncogene (33) and graft versus host disease (GvHD) and on-target/off-organ cytotoxicity (34). Selective uptake of DNA replication chain terminator drugs by engineered nucleoside kinases such as native or modified herpes-simplex-virus-thymidine-kinase (sr39TK) (35), initiation of apoptosis mediated by inducible caspase systems by chemical dimerizers (36, 37), or surface proteins designed as antibody targets (38) have all been used to eliminate gene-modified cells. sr39TK (39) is advantageous over other modalities in that it additionally serves as a positron emission tomography (PET) reporter gene, allowing in vivo imaging to non-invasively track gene modified cells using radio-labeled substrates such as 9-(4-[$^{18}$F]-fluoro-3-[hydroxymethyl]butyl)guanine ([$^{18}$F]-FHBG) (40). Despite clear potential benefit, the characterization of the utility of sr39TK as both a PET reporter and suicide gene in human HSCs and their progeny has yet to be demonstrated.

Here we report the use of a lentiviral vector encoding sr39TK to gene-modify human HSCs, demonstrate a lack of developmental skewing due to the transgene; visualization of gene-modified HSCs and their progeny at high resolution serial scans in vivo; and the ablation of gene-modified cells in hematopoietic tissues after a single course of the pro-drug GCV as evaluated by biochemical, cell-biological, and molecular biological techniques. These results lend support for the inclusion of sr39TK in clinical trials for the modification of HSCs with a cancer-antigen reactive TCR or CAR to both monitor successful transplant and provide a safety-feature allowing the ablation of cells during a serious adverse event.

Materials and Methods
HSC Transduction

Cells were thawed in a 37° C. water bath and transferred to 50 ml tubes. X-VIVO-15 was added drop-wise with agitation to dilute thawed cell product 1:10. Cells were spun at 500 g for 5 min and supernatant was aspirated. Cells were resuspended in 50 ml X-VIVO-15 and counted using a ViCELL Cell Viability Analyzer (Beckman Coulter, Brea, Calif.). Cells were spun down at 500 g for 5 min, and supernatant was aspirated. Cells were resuspended in X-VIVO-15+[50 ng/ml] SCF, [50 ng/ml] Flt3-L, [50 ng/ml] TPO, and [20 ng/ml] IL-3 (Peprotech, Rocky Hill, N.J.) at a density of 4×10^6 cells/ml. Twenty-four-well non-tissue-culture treated plates coated with RetroNectin (TaKaRa, Shiga, Japan) were seeded with 0.25 ml (1.0×10^6 cells) of cell suspension and incubated overnight. The following day, concentrated NY-ESO-1-TCR/sr39TK lentiviral prep was added for a final vector concentration of 1.0×10^8 TU/ml in a final volume of 500 ul X-VIVO-15+ cytokines as described above. Cells were incubated overnight. The following day, cells were collected from wells and rinsed thrice in X-VIVO-15 without cytokines. Cells were counted, and resuspended at a density of 2.0×10^7 cells/ml in X-VIVO-15+ cytokines as described above.

Generation of Humanized Mice

Humanized mice were generated by the intrahepatic transfer of 1.0×10^6 NY-ESO-1-TCR/sr39TK- or mock-transduced CD34+ PBSCs to neonatal NSG-HLA-A2.1 mice on day 3-5 post-birth using a 28 G tuberculin syringe (18). Neonates were preconditioned immediately before injection with 100 cGy irradiation from a $^{137}$Cs source (J L Shepherd, San Fernando, Calif.). For tissue harvest, animals were euthanized by 5% CO2 asphyxiation immediately before dissection. Single cell suspensions of thymus and spleen were prepared by dissociating organs with a 3 ml syringe plunger over 70 um mesh in FACS buffer (DPBS, 2% FBS, 2 mM EDTA). Individual bones (femurs, humeri, and sternum) were kept separate to investigate potential differences in marrow spaces by flow cytometry and ddPCR. Marrow spaces were flushed with a 23 G needle through 70 uM mesh. Cells were enumerated and 1×10^6 splenocytes, 1×10^6 cells from the marrow, and 1×10^5 thymocytes were stained with antibodies as described below. Immunological cytotoxicity assays were performed as previously described (41).

Flow Cytometry

Blood was drawn from the retro-orbital sinus using heparin coated capillary tubes (Thermo Fisher, Waltham, Mass.). The following antibodies (Becton Dickinson (BD), Laguna Hills, Calif.) were used to assess human engraftment: murine CD45-V500 clone 30-F11, human CD45-V450 clone HI30, human CD19-PE-Cy7 clone SJ25C1, human CD3-PerCP clone SK7, human CD4-APC clone RPA-T4, and human CD8-FITC clone HIT8a. Expression of the NY-ESO-1-TCR was determined by binding to a PE-labeled HLA-A2.1 MHC-tetramer loaded with the $_{157-165}$NY-ESO-1 SLLMWITQC (SEQ ID NO: 6) (Beckman Coulter, Brea, Calif.). Antibodies were added to 80 ul whole blood, incubated in the dark for 30 min, RBC lysed with 1 ml FACS Lyse (BD), washed with 3 ml FACS buffer, spun at 500 g for 5 min, and resuspended in 250 ul FACS buffer. Data were acquired on a FACS Fortessa (BD). Analysis was performed on an average of 2,000 to 10,000 hCD45+ cells per 80 ul peripheral blood drawn per mouse.

PET Scan

[$^{18}$F]-FHBG was synthesized as described (42). Mice were injected IV with 250 μCi [$^{18}$F]-FHBG in 50-100 ul, and allowed a 3 h conscious uptake. Mice were anesthetized with 2% isoflurane for sequential imaging in the Siemens Preclinical Solutions MicroPET Focus 220 and MicroCAT IICT (Siemens Malvern, Pa.). PET data were acquired for 10 min and reconstructed with a filtered background projection probability algorithm. PET/CT images were co-registered. Quantification of PET signal was performed by drawing 3D regions of interest (ROIs) using AMIDE software (http://amide.sourceforge.net/). MAP projections were generated for display in figures. The max intensity of the muscle ROI, based on the percent injected dose per gram, was subtracted from each hematopoietic niche ROI to normalize for background. Images are presented in false-color volumetric renderings generated in AMIDE.

Statistical Analysis

Descriptive statistics for quantitative variables such as the mean and standard error by experimental groups were summarized and presented. Differences between experimental groups were assessed by unpaired t-test (FIGS. 6A-6G) or pairwise comparison (FIGS. 10A-10G) within the framework of one-way analysis of variance (ANOVA). To account for variation from individual animals, linear mixed effect models with random intercept (43) were used to evaluate the between-experimental group difference (FIGS. 9A-9C, FIGS. 10E-10F) as well as pre- and post-treatment difference (FIGS. 9A-9C). For all statistical investigations, tests for significance were 2-tailed unless otherwise specified. A p-value less than the 0.05 significance level was considered to be statistically significant. All statistical analyses were performed using SAS version 9.3 (SAS, Cary, N.C.).

Results

NY-ESO-1-TCR/sr39TK Modified Human HSCs Engraft in NSG-A2.1 Mice and Generate Functional NY-ESO-1 Reactive T-Cells In Vivo To test the function of sr39TK, we generated a lentiviral vector composed of a codon optimized NY-ESO-1-TCR linked by a 2 A cleavage-peptide to sr39TK (ESO/TK) driven by the strong retroviral long-terminal-repeat promoter MSCV (FIG. 5A). Humanized mice were generated by transplanting neonatal NSG-A2.1 mice with ESO/TK transduced CD34 enriched peripheral blood stem cells (PBSC) via intrahepatic injection (FIG. 5B). At two months post-transplant, mice were screened by peripheral blood immunophenotyping. Human cell chimerism in the mice was determined by evaluating lymphocytes for human CD45% divided by total (human+murine) CD45%. Human cells were gated into hCD19+ΩB-cells and hCD3+ T-cells, and the CD3+ population was sub-fractioned to CD4 helper and CD8 cytotoxic subsets with the NY— ESO-1 tetramer binding activity of each assayed (FIG. 5C). The transplant of PBSCs to neonatal NSG-A2.1 mice resulted in human chimerism in peripheral blood beginning at 2 months post-transplant. The transduction of PBSCs with an ESO/TK lentiviral vector did not result in a significant change in total human cell chimerism nor alter the composition of human lymphoid cells (FIGS. 6A-E and Table 1). NY-ESO-1-TCR+ cells, identified by co-staining with the $_{157-165}$NY-ESO-1 HLA-A2.1 tetramer, were only observed in the animals transplanted with gene-modified cells. CD4+ T-cells bearing NY-ESO-1-TCR were not observed (FIG. 6F). CD8+NY-ESO-1-TCR bearing cells developed solely in the ESO/TK-transduced group, and 8 out of 15 mice had readily detectable TCR-positive CD8 T-cells in the periphery as early as 2 months post-transplant (FIG. 6G).

To validate the effector function of NY-ESO-1-TCR bearing T cells developed in vivo from transduced HSCs, experimental mice were harvested, splenocytes dissociated, and expanded by co-culture with artificial antigen presenting cells loaded with the $_{157-165}$NY-ESO-1 peptide. Controls were generated from healthy adult donor peripheral blood T-cells activated by CD3/CD28 beads and transduced with the ESO/TK vector or mock transduced. Ex vivo expanded splenocytes from humanized mice or control human T-cells were co-cultured with non-HLA-A2.1 (M257) or HLA-A2.1 (M257/A2.1 and M407) patient derived melanoma cell lines expressing the NY-ESO-1 antigen. $^{51}$Chromium release assays to assess cytotoxicity revealed humanized mouse derived T-cells killed target cells in an HLA-restricted fashion (FIG. 7A, 7B), comparable to control normal donor T-cells transduced with the NY-ESO-1-TCR (FIG. 7C). Minimal background cytotoxicity in non-transduced donor T-cells was observed (FIG. 7D). ELISA assays revealed similar results, with both humanized mouse derived- and healthy donor transduced NY-ESO-1 antigen-specific T-cells secreting the effector cytokine interferon-gamma when cultured in the presence of target cells (FIG. 7E).

A subset of mice were selected for PET imaging studies (non-transduced humanized N=3, ESO/TK-transduced humanized N=10) based on equivalent human chimerism and lymphocyte composition, with an additional (N=3) non-transplanted age-matched NSG-A2.1 control animals to examine background biodistribution.

sr39TK Shows Selective Uptake of [18F]-FHBG In Vivo

Figure 11B:
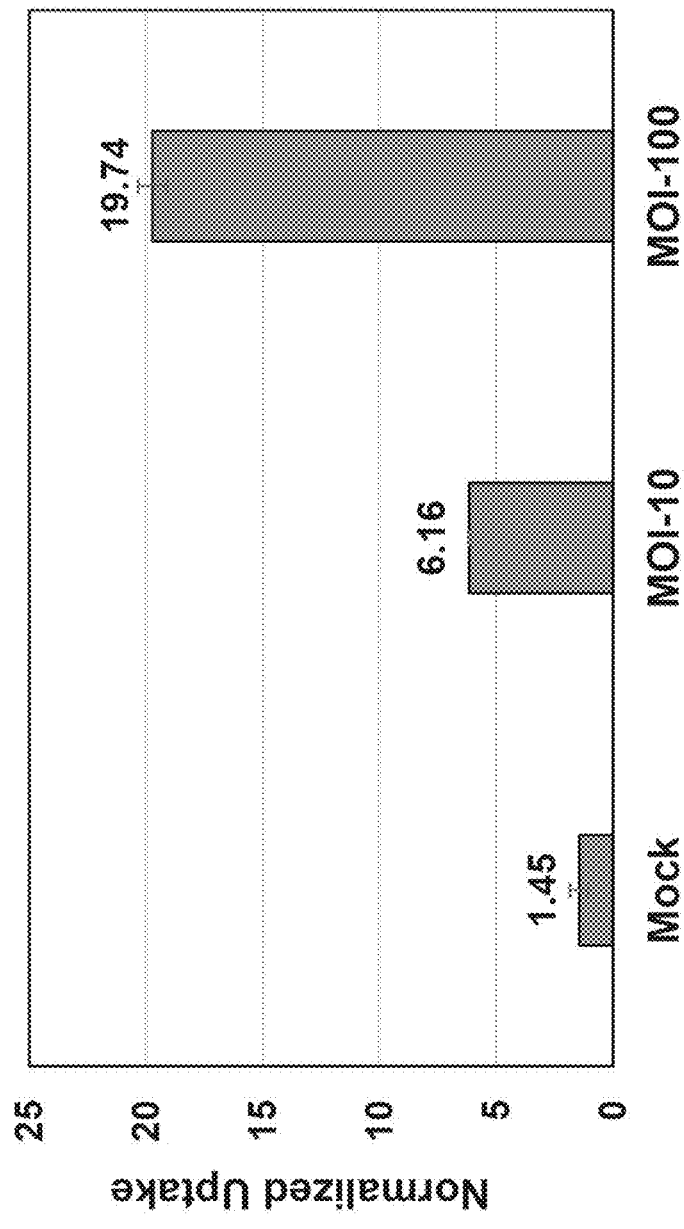
FIG. 11 shows graphs illustrating the validation of sr39TK function in Jurkat cells. (11A) Mock or ESO/TK transduced Jurkats were evaluated by flow cytometry for NY-ESO-1 tetramer binding. (11B) Cells were cultured with 0.5 μCi [$^{18}$F]-FHBG for 1 hour, washed, and evaluated for uptake. (11C) Cells were cultured in half-log increasing concentrations of GCV for 48 h and evaluated for viability.
Figure 11C:
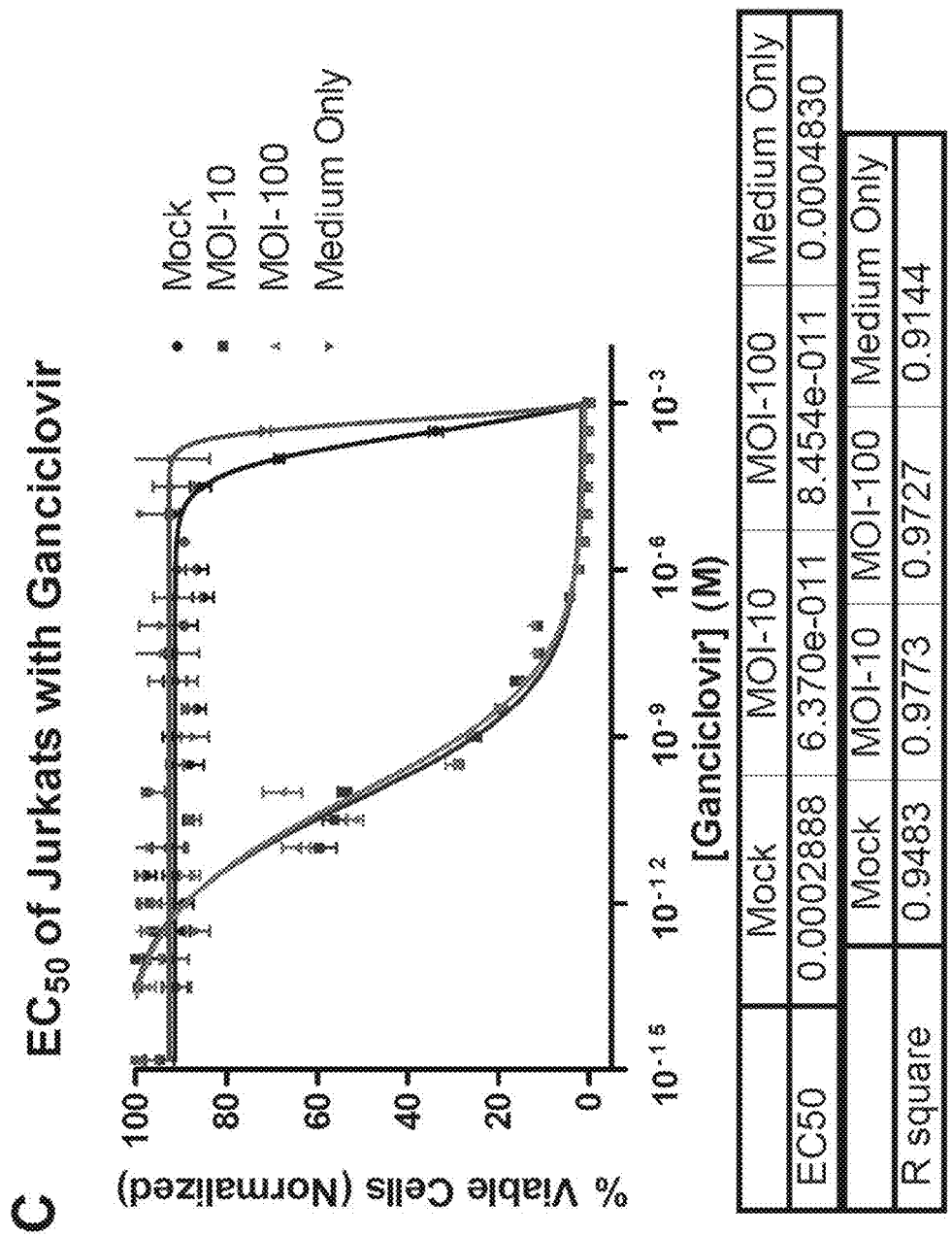

The PET reporter/suicide gene sr39TK is an engineered herpes-simplex-virus-thymidine-kinase with approximately 300× greater affinity for GCV than wild type HSV-TK (44). The ESO/TK vector was first tested in Jurkat cells in vitro. Cells transduced at an MOI of 10 and 100 expressed the NY-ESO-1-TCR (FIG. 11A), showed selective uptake of [$^{18}$F]-FHBG (FIG. 11B), and were selectively killed by GCV (FIG. 11C) confirming the functional activity of the ESO/TK vector.

To test the function of sr39TK as a PET reporter/suicide gene in vivo, we designed an experiment to serially scan humanized mice with the PET reporter [$^{18}$F]-FHBG before and after treatment with the prodrug Ganciclovir (GCV) followed by investigation of cell composition by cell- and molecular-biological methods (FIG. 7A). Non-transplanted NSG-A2.1 mice and transplant recipients of mock transduced or ESO/TK gene-modified human PBSC were injected with 250 µCi [$^{18}$F]-FHBG and imaged on a Siemens MicroPET scanner followed by CT scan for overlay. Non-transplanted NSG-A2.1 mice were imaged to determine background biodistribution of [$^{18}$F]-FHBG, which is known to have a high background in the abdominal area due to the probe elimination through the biliary tree and the GI tract in mice (45). As expected, non-humanized NSG-A2.1 mice exhibited predominantly gastrointestinal tract (GI), gall bladder, and bladder signal, with no signal in presumptive hematopoietic niches, or areas of high metabolic activity such as the brain or heart (FIG. 7B). Evaluation of uptake in the spleen was occluded by GI signal. Non-transduced humanized mice showed similar background biodistribution of [$^{18}$F]-FHBG probe, and lack of hematopoietic niche signal (FIG. 7C). In contrast, mice humanized with ESO/TK transduced PBSCs exhibited strong signal in hematopoietic compartments (i.e. long bones, skull, vertebrae, and thymus) in addition to background GI biodistribution (FIG. 7D). Signal quantitation was performed in Amide software by drawing 3-dimensional regions of interest (ROI) on individual femurs, humeri, the thymus, and arm muscle (FIG. 12A). The maximum percent injected dose/g (% ID/g) was determined for each ROI, and muscle was subtracted from hematopoietic niche ROIs to normalize background tissue uptake. Significant accumulation of probe in ROIs was observed in hematopoietic compartments in the ESO/TK-transduced cohort vs. the non-transduced humanized group (FIG. 12B).

Gene-Modified Cells are Selectively Ablated by GCV

To test the suicide gene function of sr39TK in transduced human cells in vivo, previously scanned non-transduced humanized mice and ESO/TK-transduced humanized mouse cohorts were treated intraperitoneally for 5 days with vehicle or [50 mg/kg] of the nucleoside prodrug GCV which is converted to a cytotoxic nucleotide when phosphorylated by sr39TK. PET/CT imaging was performed one week after the final drug injection to allow ablation of gene-modified cells and clearance of residual GCV. Vehicle treated ESO/TK mice demonstrated specific uptake in hematopoietic niches in pre- and post-treatment scans (FIG. 8A); however, GCV completely ablated PET signal in post-treatment scans in all hematopoietic niches previously observed to harbor probe accumulation in ESO/TK-transduced humanized mice (FIG. 8B). No difference in signal accumulation was detected in pre- and post-treatment scans in the non-transduced humanized cohort (FIG. 12C). Vehicle treated ESO/TK-transduced recipient mice showed no significant difference in signal accumulation in hematopoietic compartments as determined by pre- and post-treatment scans (FIG. 8C). GCV treated ESO/TK-transduced recipient mice showed significant ablation of [$^{18}$F]-FHBG PET signal in hematopoietic compartments in post-treatment scans (FIG. 8D). The post-treatment signal of GCV treated ESO/TK mice were not significantly different than background uptake in non-transduced humanized mice.

Animals were euthanized one day after the final scan, and tissues were collected and dissociated. Cell suspensions were enumerated, and allocated for subsequent analyses. Flow cytometry of splenocytes to measure chimerism revealed human cells present in all cohorts; non-transduced humanized, vehicle treated- and GCV-treated ESO/TK-transduced humanized mice. There was not a significant reduction of human chimerism in GCV treated ESO/TK mice (FIG. 9A). CD19 B-cells and CD3 T-cells were detected in all cohorts at endpoint analysis with no significant difference between vehicle and GCV treated ESO/TK mice (FIGS. 9B,C). In contrast, NY-ESO-1-TCR bearing CD3+CD8+ T-cells were reduced to background levels in the GCV treated ESO/TK-transduced humanized mice (FIG. 9D).

Quantitation of PET signal and flow cytometric analyses demonstrated ablation of gene-modified cells while sparing non-modified cells. However, cells with low metabolic activity may not be sensitive to drug selection nor show specific uptake of [$^{18}$F]-FHBG. In addition, as surface TCR expression requires co-expression of CD3, flow cytometry is unable to measure the presence of this transgene in non-T-cells. In order to investigate persistence of other gene-modified cells, quantitative PCR was performed to measure the amount of lentiviral vector psi element per human genome in each organ compartment. No vector genomes were detected in non-transduced humanized mice (FIG. 9E). The amount of vector present in the ESO/TK-transduced mice treated with vehicle varied among different animals (mean=0.918±0.131, range=0.552-1.72), but was relatively consistent among the different tissues tested for each recipient (FIG. 9F). In the cohort treated with a course of GCV, there was a significant reduction of integrated vector (mean=0.123±0.131) compared with the vehicle treated cohort (FIG. 9G) ($P<0.001$).

Discussion

Gene therapy using HSCs has proven to be an efficacious treatment for monogenetic diseases, and is currently of interest for immunotherapy applications. Pre-clinical studies have provided evidence that HSCs transduced to express a transgenic TCR are capable of producing antigen specific effector T-cells in vivo paving the way for a first-in-man study nearing Phase I clinical trial (CIRM Disease Team Grant DR2A-05309). However, several questions remain. Enthusiasm for engineered immunity is tempered by the possibility of on-target/off-organ reactivity of the modified cells, and the cautionary tales of clonal outgrowth in HSC gene therapy patients merit the inclusion of safety measures in vector design. The inclusion of a suicide gene could provide a safety switch capable of ablating gene-modified cells in the event of undesirable off-target reactivity or clonal transformation. The ability to non-invasively track gene-modified cells in vivo would allow early detection of successful engraftment, active thymopoiesis, and homing to tumor tissue.

The humanized mouse allows the study of HSCs and development of their progeny in vivo. We used this model system to investigate the potential application of the PET reporter/suicide gene sr39TK in the setting of HSC based engineered immunotherapy to non-invasively locate and ablate gene modified cells. We observed no detrimental effect of lentiviral transduction with the ESO/TK vector on the engraftment of PBSCs as evidenced by equivalent human chimerism and lymphoid composition between transduced and mock transduced cohorts. Detection of gene-modified cells by PET was ubiquitous in ESO/TK transduced humanized mice (N=15), though only 8/15 (53.33%) had detectable NY-ESO-1-TCR+ cells in peripheral blood at 2-months post-transplant. Therefore, PET imaging allowed early assessment of engraftment of gene-modified cells before NY-ESO-1-TCR+ cells have developed and migrated to the periphery in sufficient numbers for flow cytometric analysis.

A previous report used bioluminescent imaging and the luciferase reporter to visualize gene-modified human HSCs and their progeny residing in hematopoietic niches in a humanized mouse model (46). Our work expands on this pioneering study by using PET imaging, a higher-resolution, directly clinically translatable approach to locate human HSCs in vivo. HSCs modified to express sr39TK were observed in hematopoietic niches, such as the long bones of the arms and legs and the thymus after dosing with [$^{18}$F]-FHBG. Strong sternal signal in mice led us to include this hematopoietic niche in our harvests, a practice not routinely performed in humanized mouse studies yet an abundant source of hematopoietic cells. Punctate murine vertebral marking with engraftment of vector-bearing cells (FIG. 13) directly demonstrates the high-resolution possible with this imaging technology. The limit of detection using [$^{18}$F]-FHBG as a probe with the HSV-sr39TK PET reporter gene was previously determined to be $1\times10^{\wedge}6$ cells/mm$^{\wedge}3$(47). The thymus of a well-engrafted humanized mouse is populated by approximately $2.5\times10^{\wedge}6$ human thymocytes, the majority of which are TCR positive in transduced cohorts, and is approximately 1 mm$^{\wedge}3$ in volume (EHG unpublished observation). In the clinical setting, the number of transduced cells along with the richer soil of a human host for transduced/transplanted human HSCs is likely to result in robust PET imaging in excess of seen in our humanized mouse study.

While the immunogenicity of sr39TK has been reported in human studies of gene modified T-cells (48, 49), in the setting of gene modified HSCs, de novo generated DCs may home to the thymus and induce tolerance to the introduced gene product (50). Currently, only in silico predictive models of human immunogenicity exist, and the only true test is to evaluate the development of an immune reaction to a transgene in clinical trials. Still, there are alternative approaches that do not rely on viral-derived or otherwise xenogeneic reporter genes (37, 51).

Although PET signal was completely ablated after GCV treatment, we detected a small amount of vector-containing cells in harvested hematopoietic compartments by qPCR. This may indicate that some transduced HSCs were GCV resistant and generated new cells post-GCV treatment. Longitudinal studies to examine these possibilities in small animals are technically difficult owing to the paucity of human cells generated, though a recent study examining sr39TK mediated ablation of rhesus macaque HSCs provides evidence that a single round of GCV is sufficient to ablate stem cells (52). The elimination of the majority of modified cells should be sufficient to control major toxicities.

sr39TK allows evaluation of successful engraftment of gene-modified HSCs in vivo with high resolution, and the detection of thymic engraftment indicative of developing anti-cancer TCR expressing T-cells. It may further be used to examine the homing of gene-modified T-cells to intended tumor targets and eradication of disease. In the event of off-target cytotoxicity by engineered T-cells, GvHD, or insertional oncogenesis, the suicide gene function of sr39TK could be harnessed to eliminate modified cells while importantly sparing the remaining unmodified graft. Our study supports the hypothesis that a clinical approach to engineered HSC immunotherapy would benefit from the inclusion of an imaging/suicide gene.

Example 2: Supplemental Methods

NY-ESO-1-TCR/sr39TK Vector Cloning and Virus Production

The TCR recognizing the NY-ESO-1 cancer/testes antigen has been previously described (53). Modifications to this self-inactivating (SIN) lentiviral vector include codon optimization of the 2A-linked TCR alpha and beta cDNA and 2 A linkage to a codon-optimized sr39TK sequence, internal Murine Stem Cell Virus (MSCV) LTR promoter, and the WPRE (ESO/TK). Large-scale manufacture of concentrated lentivirus using a $2^{nd}$ generation self-inactivating HIV-1 vector system was performed as described previously (54). Briefly, 239T cells were transfected with (150 ug) ESO/TK transfer plasmid, (150 ug) p8.9 HIV-1 gag-pol expression plasmid, and (30 ug) pMD-G VSV-G expression plasmid. One day following transfection, sodium butyrate induction was performed for 8 h. Viral supernatant was harvested on d4 and d5 of production, followed by 2000-fold concentration by tangential flow filtration (SpectrumLabs, CA) with diafiltration to 10% X-VIVO-15 medium (Lonza, Walkersville, Md.). qPCR titers on HT29 cells of concentrated preps ranged from $7.6 \times 10^{\wedge}8$ TU/ml-$4.0 \times 10^{\wedge}9$ TU/ml.

NSG-A2.1 Mice

NSG mice harboring a transgene encoding the human HLA-A2.1 protein covalently linked to human beta 2 microglobulin (NOD.Cg-Prkdcscid Il2rgtmlWjl Tg(HLA-A/H2-D/B2M)1Dvs/SzJ, Stock number 014570) were obtained from The Jackson Laboratory (Bar Harbor, Me.) (55). Mice were bred, housed, and monitored according to UCLA Department of Laboratory Animal Medicine standards.

Transduction of Jurkat Cells and Uptake Assay

Jurkat cells (ATCC TIB-152) were transduced with the ESO/TK lentiviral vector at an MOI of 10 and 100, cultured for 2 weeks, and assayed for surface TCR expression by tetramer staining to validate transduction. Mock transduced, MOI-10 and MOI-100 transduced Jurkats were cultured in 0.5 µCi [$^{18}$F]-FHBG for 1 hr, cells were washed 3×, and resuspended in 1ml culture medium. Uptake was measured on a Wallac WIZARD scintillation counter (Perkin Elmer, Waltham, Mass.) using RiaCalc WIZ software (Perkin Elmer).

HSC Isolation and Purification

G-CSF mobilized peripheral blood units were purchased from Cincinnati Children's Hospital Medical Center and processed with the CliniMACS CD34 Reagent System, CD34 Kit, and Tubing System (Miltenti, Auburn, Calif.) per manufacturer's instructions. Approximately $3.44 \times 10^{\wedge}9$ CD34+ cells were obtained from approximately 150 ml apheresis product at a purity of >98% as assessed by flow cytometry. Aliquots of $5.0 \times 10^{\wedge}6$ cells were frozen in Pentastarch+10% DMSO at −80C overnight then transferred to liquid nitrogen for long-term storage.

VCN Analysis

Vector copy number was determined by digital droplet quantitative PCR (ddPCR) for the lentiviral psi element (FWD: AAG TAG TGT GTG CCC GTC TG (SEQ ID NO: 7), REV: CCT CTG GTT TCC CTT TCG CT (SEQ ID NO: 8), PRO: 5'-FAM/CCC TCA GAC/ZEN/CCT TTT AGT) and normalized to the endogenous human SDC4 reference gene (FWD: CAG GGT CTG GGA GCC AAG T (SEQ ID NO: 9), REV: GCA CAG TGC TGG ACA TTG ACA (SEQ ID NO: 10), PRO: 5'-HEX/CCC ACC GAA CCC AAG AAA CTA (SEQ ID NO: 11)). Genomic DNA was extracted using the NucleoSpin Tissue kit (Macherey Nagel, Bethlehem, Pa.). PCR using 200 ng genomic DNA template, [400 nM] primers and [100 nM] probe, and 1000 U DraI per reaction was digested for 1 hr at 37 C. Digested pre-PCR reactions were run through the QX100 Droplet Generator (BioRad, Hercules, Calif.) followed by the following reaction conditions: 95C for 10 min, [94C for 30 sec, 60C for 1 min] for 55 cycles, 98C for 10 min, and 12 C hold on a T100 thermal cycler (BioRad). Droplets were read on a QX100 Droplet Reader (BioRad).

TABLE 1

Total human chimerism and lymphoid composition in NSG recipients of ESO/TK-transduced or non-transduced PBSC.

| | Non-Transduced | ESO/TK-Transduced |
|---|---|---|
| Total PB Chimerism (% of lymphocytes) | 35.44 ± 10.60% | 32.00 ± 2.97% |
| CD19+ B Cells | 70.94 ± 15.09% | 69.47 ± 6.24% |
| CD3+ T Cells | 7.70 ± 5.55% | 8.49 ± 4.03% |
| % CD4+/CD3+ T Cells | 22.36 ± 8.09% | 35.67 ± 10.23% |
| % CD8+/CD3+ T Cells | 19.74 ± 6.63% | 31.59 ± 4.93% |

REFERENCES

Note: This application references a number of different publications as indicated throughout the specification by reference numbers enclosed in parenthesis, e.g., (x). A list of these different publications ordered according to these reference numbers can be found below.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further, the actual publication dates may be different from those shown and require independent verification.

1. Bordignon C, Notarangelo L D, Nobili N, et al. Gene therapy in peripheral blood lymphocytes and bone marrow for ADA-immunodeficient patients. Science (New York, N.Y.). 1995 Oct. 20; 270(5235):470-5.
2. Kohn D B, Weinberg K I, Nolta J A, et al. Engraftment of gene-modified umbilical cord blood cells in neonates with adenosine deaminase deficiency. Nature medicine. 1995 October; 1(10):1017-23.

3. Aiuti A, Slavin S, Aker M, et al. Correction of ADA-SCID by stem cell gene therapy combined with nonmyeloablative conditioning. Science (New York, N.Y.). 2002 Jun. 28; 296(5577):2410-3.
4. Wirth T, Parker N, Yla-Herttuala S. History of gene therapy. Gene. 2013 Aug. 10; 525(2):162-9.
5. Morgan R A, Dudley M E, Wunderlich J R, et al. Cancer regression in patients after transfer of genetically engineered lymphocytes. Science (New York, N.Y.). 2006 Oct. 6; 314(5796):126-9.
6. Grupp S A, Kalos M, Barrett D, et al. Chimeric antigen receptor-modified T cells for acute lymphoid leukemia. The New England journal of medicine. 2013 Apr. 18; 368(16):1509-18.
7. Brentjens R J, Davila M L, Riviere I, et al. CD19-targeted T cells rapidly induce molecular remissions in adults with chemotherapy-refractory acute lymphoblastic leukemia. Science translational medicine. 2013 Mar. 20; 5(177): 177ra38.
8. Robbins P F, Morgan R A, Feldman S A, et al. Tumor regression in patients with metastatic synovial cell sarcoma and melanoma using genetically engineered lymphocytes reactive with N Y-ESO-1. Journal of clinical oncology: official journal of the American Society of Clinical Oncology. 2011 Mar. 1; 29(7):917-24.
9. Gattinoni L, Klebanoff C A, Palmer D C, et al. Acquisition of full effector function in vitro paradoxically impairs the in vivo antitumor efficacy of adoptively transferred CD8+ T cells. The Journal of clinical investigation. 2005 June; 115(6):1616-26.
10. Zhou J, Shen X, Huang J, Hodes R J, Rosenberg S A, Robbins P F. Telomere length of transferred lymphocytes correlates with in vivo persistence and tumor regression in melanoma patients receiving cell transfer therapy. Journal of immunology (Baltimore, Md.: 1950). 2005 Nov. 15; 175(10):7046-52.
11. Ma C, Cheung A F, Chodon T, et al. Multifunctional T-cell analyses to study response and progression in adoptive cell transfer immunotherapy. Cancer discovery. 2013 April; 3(4):418-29.
12. Gattinoni L, Klebanoff C A, Restifo N P. Paths to sternness: building the ultimate antitumour T cell. Nature reviews Cancer. 2012 October; 12(10):671-84.
13. Gattinoni L, Restifo N P. Moving T memory stem cells to the clinic. Blood. 2013 Jan. 24; 121(4):567-8.
14. Cieri N, Camisa B, Cocchiarella F, et al. IL-7 and IL-15 instruct the generation of human memory stem T cells from naive precursors. Blood. 2013 Jan. 24; 121(4):573-84.
15. Terakura S, Yamamoto T N, Gardner R A, Turtle C J, Jensen M C, Riddell S R. Generation of CD19-chimeric antigen receptor modified CD8+ T cells derived from virus-specific central memory T cells. Blood. 2012 Jan. 5; 119(1):72-82.
16. Wang X, Berger C, Wong C W, Forman S J, Riddell S R, Jensen M C. Engraftment of human central memory-derived effector CD8+ T cells in immunodeficient mice. Blood. 2011 Feb. 10; 117(6):1888-98.
17. Yang L, Baltimore D. Long-term in vivo provision of antigen-specific T cell immunity by programming hematopoietic stem cells. Proceedings of the National Academy of Sciences of the United States of America. 2005 Mar. 22; 102(12):4518-23.
18. Giannoni F, Hardee C L, Wherley J, et al. Allelic exclusion and peripheral reconstitution by TCR transgenic T cells arising from transduced human hematopoietic stem/progenitor cells. Molecular therapy: the journal of the American Society of Gene Therapy. 2013 May; 21(5):1044-54.
19. Vatakis D N, Koya R C, Nixon C C, et al. Antitumor activity from antigen-specific CD8 T cells generated in vivo from genetically engineered human hematopoietic stem cells. Proceedings of the National Academy of Sciences of the United States of America. 2011 Dec. 20; 108(51):E1408-16.
20. Vatakis D N, Arumugam B, Kim S G, Bristol G, Yang O, Zack J A. Introduction of exogenous T-cell receptors into human hematopoietic progenitors results in exclusion of endogenous T-cell receptor expression. Molecular therapy: the journal of the American Society of Gene Therapy. 2013 May; 21(5):1055-63.
21. De Oliveira S N, Ryan C, Giannoni F, et al. Modification of Hematopoietic Stem/Progenitor Cells with CD19-Specific Chimeric Antigen Receptors as a Novel Approach for Cancer Immunotherapy. Human gene therapy. 2013 October; 24(10):824-39.
22. Gaspar H B, Cooray S, Gilmour K C, et al. Long-term persistence of a polyclonal T cell repertoire after gene therapy for X-linked severe combined immunodeficiency. Science translational medicine. 2011 Aug. 24; 3(97): 97ra79.
23. Candotti F, Shaw K L, Muul L, et al. Gene therapy for adenosine deaminase-deficient severe combined immune deficiency: clinical comparison of retroviral vectors and treatment plans. Blood. 2012 Nov. 1; 120(18):3635-46.
24. Hacein-Bey-Abina S, von Kalle C, Schmidt M, et al. A serious adverse event after successful gene therapy for X-linked severe combined immunodeficiency. The New England journal of medicine. 2003 Jan. 16; 348(3):255-6.
25. Emery D W. The use of chromatin insulators to improve the expression and safety of integrating gene transfer vectors. Human gene therapy. 2011 June; 22(6):761-74.
26. Yu S F, von Ruden T, Kantoff P W, et al. Self-inactivating retroviral vectors designed for transfer of whole genes into mammalian cells. Proceedings of the National Academy of Sciences of the United States of America. 1986 May; 83(10):3194-8.
27. Zufferey R, Dull T, Mandel R J, et al. Self-inactivating lentivirus vector for safe and efficient in vivo gene delivery. Journal of virology. 1998 December; 72(12):9873-80.
28. Miyoshi H, Blomer U, Takahashi M, Gage F H, Verma I M. Development of a self-inactivating lentivirus vector. Journal of virology. 1998 October; 72(10):8150-7.
29. Morgan R A, Yang J C, Kitano M, Dudley M E, Laurencot C M, Rosenberg S A. Case report of a serious adverse event following the administration of T cells transduced with a chimeric antigen receptor recognizing ERBB2. Molecular therapy: the journal of the American Society of Gene Therapy. 2010 April; 18(4): 843-51.
30. Porter D L, Levine B L, Kalos M, Bagg A, June C H. Chimeric antigen receptor-modified T cells in chronic lymphoid leukemia. The New England journal of medicine. 2011 Aug. 25; 365(8):725-33.
31. Johnson L A, Morgan R A, Dudley M E, et al. Gene therapy with human and mouse T-cell receptors mediates cancer regression and targets normal tissues expressing cognate antigen. Blood. 2009 Jul. 16; 114(3):535-46.
32. Linette G P, Stadtmauer E A, Maus M V, et al. Cardiovascular toxicity and titin cross-reactivity of affinity-enhanced T cells in myeloma and melanoma. Blood. 2013 Aug. 8; 122(6):863-71.

33. Blumenthal M, Skelton D, Pepper K A, Jahn T, Methangkool E, Kohn D B. Effective suicide gene therapy for leukemia in a model of insertional oncogenesis in mice. Molecular therapy: the journal of the American Society of Gene Therapy. 2007 January; 15(1):183-92.
34. Bonini C, Ferrari G, Verzeletti S, et al. HSV-T K gene transfer into donor lymphocytes for control of allogeneic graft-versus-leukemia. Science (New York, N.Y.). 1997 Jun. 13; 276(5319):1719-24.
35. Black M E, Newcomb T G, Wilson H M, Loeb L A. Creation of drug-specific herpes simplex virus type 1 thymidine kinase mutants for gene therapy. Proceedings of the National Academy of Sciences of the United States of America. 1996 Apr. 16; 93(8):3525-9.
36. Straathof K C, Pule M A, Yotnda P, et al. An inducible caspase 9 safety switch for T-cell therapy. Blood. 2005 Jun. 1; 105(11):4247-54.
37. Di Stasi A, Tey S K, Dotti G, et al. Inducible apoptosis as a safety switch for adoptive cell therapy. The New England journal of medicine. 2011 Nov. 3; 365(18):1673-83.
38. Wang X, Chang W C, Wong C W, et al. A transgene-encoded cell surface polypeptide for selection, in vivo tracking, and ablation of engineered cells. Blood. 2011 Aug. 4; 118(5):1255-63.
39. Qasim W, Thrasher A J, Buddle J, Kinnon C, Black M E, Gaspar H B. T cell transduction and suicide with an enhanced mutant thymidine kinase. Gene therapy. 2002 June; 9(12):824-7.
40. Gambhir S S, Bauer E, Black M E, et al. A mutant herpes simplex virus type 1 thymidine kinase reporter gene shows improved sensitivity for imaging reporter gene expression with positron emission tomography. Proceedings of the National Academy of Sciences of the United States of America. 2000 Mar. 14; 97(6):2785-90.
41. Ribas A, Butterfield L H, Hu B, et al. Generation of T-cell immunity to a murine melanoma using MART-1-engineered dendritic cells. Journal of immunotherapy (Hagerstown, Md.: 1997). 2000 January; 23(1):59-66.
42. Alauddin M M, Conti P S. Synthesis and preliminary evaluation of 9-(4418F1-fluoro-3-hydroxymethylbutyl) guanine ([18F]FHBG): a new potential imaging agent for viral infection and gene therapy using PET. Nuclear medicine and biology. 1998 April; 25(3):175-80.
43. Laird N M, Ware J H. Random-effects models for longitudinal data. Biometrics. 1982 December; 38(4):963-74.
44. Black M E, Kokoris M S, Sabo P. Herpes simplex virus-1 thymidine kinase mutants created by semi-random sequence mutagenesis improve prodrug-mediated tumor cell killing. Cancer research. 2001 Apr. 1; 61(7):3022-6.
45. Yaghoubi S, Barrio J R, Dahlbom M, et al. Human pharmacokinetic and dosimetry studies of [(18)F]FHBG: a reporter probe for imaging herpes simplex virus type-1 thymidine kinase reporter gene expression. Journal of nuclear medicine: official publication, Society of Nuclear Medicine. 2001 August; 42(8):1225-34.
46. Wang X, Rosol M, Ge S, et al. Dynamic tracking of human hematopoietic stem cell engraftment using in vivo bioluminescence imaging. Blood. 2003 Nov. 15; 102(10):3478-82.
47. Su H, Forbes A, Gambhir S S, Braun J. Quantitation of cell number by a positron emission tomography reporter gene strategy. Molecular imaging and biology: MIB: the official publication of the Academy of Molecular Imaging. 2004 May-June; 6(3):139-48.
48. Riddell S R, Elliott M, Lewinsohn D A, et al. T-cell mediated rejection of gene-modified HIV-specific cytotoxic T lymphocytes in HIV-infected patients. Nature medicine. 1996 February; 2(2):216-23.
49. Berger C, Flowers M E, Warren E H, Riddell S R. Analysis of transgene-specific immune responses that limit the in vivo persistence of adoptively transferred HSV-T K-modified donor T cells after allogeneic hematopoietic cell transplantation. Blood. 2006 Mar. 15; 107(6):2294-302.
50. Fehr T, Sykes M. Tolerance induction in clinical transplantation. Transplant immunology. 2004 September-October; 13(2):117-30.
51. McCracken M N, Gschweng E H, Nair-Gill E, et al. Long-term in vivo monitoring of mouse and human hematopoietic stem cell engraftment with a human positron emission tomography reporter gene. Proceedings of the National Academy of Sciences of the United States of America. 2013 Jan. 29; 110(5):1857-62.
52. Barese C N, Krouse A E, Metzger M E, et al. Thymidine kinase suicide gene-mediated ganciclovir ablation of autologous gene-modified rhesus hematopoiesis. Molecular therapy: the journal of the American Society of Gene Therapy. 2012 October; 20(10):1932-43.
53. Robbins P F, Li Y F, El-Gamil M, et al. Single and dual amino acid substitutions in TCR CDRs can enhance antigen-specific T cell functions. Journal of immunology (Baltimore, Md.: 1950). 2008 May 1; 180(9):6116-31.
54. Cooper A R, Patel S, Senadheera S, Plath K, Kohn D B, Hollis R P. Highly efficient large-scale lentiviral vector concentration by tandem tangential flow filtration. Journal of virological methods. 2011 October; 177(1):1-9.
55. Shultz L D, Saito Y, Najima Y, et al. Generation of functional human T-cell subsets with HLA-restricted immune responses in HLA class I expressing NOD/SCID/IL2r gamma(null) humanized mice. Proceedings of the National Academy of Sciences of the United States of America. 2010 Jul. 20; 107(29):13022-7.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching.

The invention claimed is:
1. A composition of matter comprising a polynucleotide having a sequence shown in SEQ ID NO: 1.
2. The composition of matter of claim 1, further comprising a polynucleotide having a sequence shown in SEQ ID NO: 3.
3. The composition of matter of claim 2, wherein the polynucleotide having the sequence shown in SEQ ID NO: 1 and the polynucleotide having the sequence shown in SEQ ID NO: 3 are disposed within a vector adapted to express a functional T cell receptor (TCR) comprising a TCR alpha chain polypeptide shown in SEQ ID NO: 2 and a TCR beta chain polypeptide shown in SEQ ID NO: 4.
4. The composition of matter of claim 3, wherein the vector is a lentiviral vector.
5. The composition of matter of claim 4, wherein the lentiviral vector comprises:
   (a) a PET reporter gene;
   (b) a suicide gene;
   (c) a murine stem cell virus (MSCV) promoter comprising nucleotide 1955 to nucleotide 2329 of SEQ ID NO: 5;
   (d) a 3' self-inactivating (SIN) LTR comprising nucleotide 5971 to nucleotide 6204 of SEQ ID NO: 5;
   (e) a central polypurine tract (cPPT) comprising nucleotide 1809 to nucleotide 1926 of SEQ ID NO: 5;
   (f) a Rev-responsive element (RRE) comprising nucleotide 933 to nucleotide 1790 of SEQ ID NO: 5;
   (g) a 5' LTR comprising nucleotide 6 to nucleotide 415 of SEQ ID NO: 5; or
   (h) a sr39 thymidine kinase comprising nucleotide 4294 to nucleotide 5289 of SEQ ID NO: 5.
6. The composition of matter of claim 5, wherein the SIN 3' LTR comprises:
   (a) a Delta unique 3' (U3) region comprising nucleotide 5971 to nucleotide 6023 of SEQ ID NO: 5;
   (b) a redundancy (R) region comprising nucleotide 6024 to nucleotide 612 of SEQ ID NO: 5; or
   (c) a unique 5' (U5) region comprising nucleotide 6122 to nucleotide 6204 of SEQ ID NO: 5.
7. The composition of matter of claim 5, wherein the 5 'LTR comprises
   (a) a unique 3' (U3) region comprising nucleotide 6 to nucleotide 235 of SEQ ID NO: 5;
   (b) a redundancy (R) region comprising nucleotide 236 to nucleotide 332 of SEQ ID NO: 5; and
   (c) a unique 5' (U5) region comprising nucleotide 333 to nucleotide 415 of SEQ ID NO: 5.
8. A host cell transduced with the vector of claim 3, wherein the host cell is not present in a human being.
9. The host cell of claim 8, wherein the host cell is a G-CSF-mobilized peripheral blood stem cell (PBSC).
10. The host cell of claim 8, wherein the host cell kills target cells expressing a NY ESO-1 antigen.
11. A method of inhibiting the growth of a target cell expressing a NY ESO-1 antigen comprising:
   combining the target cell with a peripheral blood stem cell (PBSC) transduced with a vector comprising a polynucleotide having the sequence shown in SEQ ID NO: 1 and a polynucleotide having the sequence shown in SEQ ID NO: 3, wherein:
   continuous production of fully functional TCR transgenic lymphocytes expressing a T cell receptor (TCR) comprising a TCR alpha chain polypeptide shown in SEQ ID NO: 2 and a TCR beta chain polypeptide shown in SEQ ID NO: 4; and
   the target cell and the PBSC are combined under conditions selected to:
      allow the progeny TCR transgenic lymphocytes to recognize the target cell using the TCR alpha chain polypeptide shown in SEQ ID NO: 2 and the TCR beta chain polypeptide shown in SEQ ID NO: 4; and
      inhibit growth of the target cell,
   so that the growth of the target cell expressing the NY ESO-1 antigen is inhibited.
12. The method of claim 11, wherein the target cell and the PBSC are combined in vivo.
13. The method of claim 12, wherein the target cell and the PBSC are combined in an individual diagnosed with a pathological condition.
14. The method of claim 13, wherein the pathological condition is cancer.
15. The method of claim 12, wherein the target cell is a human cancer cell.
16. The method of claim 15, wherein the target cell is a melanoma cell.
17. The method of claim 13, wherein the individual diagnosed with a pathological condition has received chemotherapy or radiation therapy prior to combining the target cell with the PBSC.
18. The method of claim 17, wherein the individual has received a myelodepleting chemotherapy regimen prior to combining the target cell with the PBSC.
19. The method of claim 11, wherein the vector encodes a HSV1-sr39tk thymidine kinase polypeptide.
20. The method of claim 18, further comprising combining the PBSC with a positron emission tomography tracer.
21. A method of inhibiting the growth of a target cell expressing a NY ESO-1 antigen comprising:
   combining the target cell with a peripheral blood stem cell (PBSC) transduced with a vector comprising a polynucleotide having the sequence shown in SEQ ID NO: 1 and a polynucleotide having the sequence shown in SEQ ID NO: 3, wherein:
   the vector expresses a functional T cell receptor (TCR) comprising a TCR alpha chain polypeptide shown in SEQ ID NO: 2 and a TCR beta chain polypeptide shown in SEQ ID NO: 4; and
   the target cell and the PBSC are combined under conditions selected to:
      allow the PBSC to recognize the target cell using the TCR alpha chain polypeptide shown in SEQ ID NO: 2 and the TCR beta chain polypeptide shown in SEQ ID NO: 4; and
      inhibit growth of the target cell,
   so that the growth of the target cell expressing the NY ESO-1 antigen is inhibited.

* * * * *